(12) United States Patent
Park et al.

(10) Patent No.: US 9,151,714 B2
(45) Date of Patent: Oct. 6, 2015

(54) METHOD OF MANUFACTURING MICRO CHAMBER PLATE WITH BUILT-IN SAMPLE AND ANALYTIC MICRO CHAMBER PLATE, ANALYTIC MICRO CHAMBER PLATE AND APPARATUS SET FOR MANUFACTURING ANALYTIC MICRO CHAMBER PLATE WITH BUILT-IN SAMPLE

(75) Inventors: Han Oh Park, Daejeon (KR); Gu Young Song, Daejeon (KR); Jung A Bae, Daejeon (KR)

(73) Assignee: BIONEER CORPORATION, Daejeon (KR)

( * ) Notice: Subject to any disclaimer, the term of this patent is extended or adjusted under 35 U.S.C. 154(b) by 249 days.

(21) Appl. No.: 13/810,534

(22) PCT Filed: Jun. 1, 2011

(86) PCT No.: PCT/KR2011/004010
§ 371 (c)(1),
(2), (4) Date: Jan. 16, 2013

(87) PCT Pub. No.: WO2012/011660
PCT Pub. Date: Jan. 26, 2012

(65) Prior Publication Data
US 2013/0115686 A1    May 9, 2013

(30) Foreign Application Priority Data
Jul. 23, 2010  (KR) .................. 10-2010-0071651

(51) Int. Cl.
*B01L 3/00* (2006.01)
*B01L 1/00* (2006.01)
*G01N 21/64* (2006.01)
*C12M 1/32* (2006.01)

(52) U.S. Cl.
CPC ........ *G01N 21/6454* (2013.01); *B01L 3/50255* (2013.01); *B01L 3/50851* (2013.01); *C12M 23/12* (2013.01); *B01L 2200/12* (2013.01); *B01L 2200/16* (2013.01); *B01L 2300/044* (2013.01); *B01L 2300/048* (2013.01); *B01L 2300/0681* (2013.01); *B01L 2300/0829* (2013.01); *B01L 2400/0409* (2013.01); *B01L 2400/049* (2013.01); *Y10T 29/51* (2015.01); *Y10T 137/0402* (2015.04)

(58) Field of Classification Search
CPC ............ B01L 2200/12; B01L 2200/16; B01L 2300/0829
See application file for complete search history.

(56) References Cited

U.S. PATENT DOCUMENTS

| | | | |
|---|---|---|---|
| 6,544,480 B1 * | 4/2003 | Velghe et al. | ............... 422/522 |
| 2004/0100284 A1 | 5/2004 | Lee et al. | |
| 2005/0042639 A1 | 2/2005 | Knapp et al. | |
| 2008/0192254 A1 | 8/2008 | Kim et al. | |
| 2010/0184028 A1 | 7/2010 | Hsing et al. | |
| 2010/0261184 A1 | 10/2010 | Park et al. | |

* cited by examiner

*Primary Examiner* — Nathan Bowers
(74) *Attorney, Agent, or Firm* — Paratus Law Group, PLLC

(57) ABSTRACT

The present invention relates to a micro chamber plate, and more particularly, to an analytic micro chamber plate in which a plurality of reaction solutions including a primer or probe selectively reacting with a nucleic acid react with each other without cross-contamination to measure and analyze a fluorescence level in real-time so as to analyze biological sample solution including a large amount of nucleic acids. Also, the present invention relates to a method of manufacturing the analytic chamber plate. Also, the present invention relates to a method of manufacturing a micro chamber plate with a built-in sample used for manufacturing the analytic chamber plate. Also, the present invention relates to an apparatus set for manufacturing the micro chamber plate with a built-in sample.

7 Claims, 15 Drawing Sheets

METHOD OF MANUFACTURING MICRO CHAMBER PLATE WITH BUILT-IN SAMPLE AND ANALYTIC MICRO CHAMBER PLATE, ANALYTIC MICRO CHAMBER PLATE AND APPARATUS SET FOR MANUFACTURING ANALYTIC MICRO CHAMBER PLATE WITH BUILT-IN SAMPLE

CROSS REFERENCE TO PRIOR APPLICATION

This application is a National Stage Patent Application of PCT International Patent Application No. PCT/KR2011/004010 (filed on Jun. 1, 2011) under 35 U.S.C. §371, which claims priority to Korean Patent Application No. 10-2010-0071651 (filed on Jul. 23, 2010) which are all hereby incorporated by reference in their entirety.

TECHNICAL FIELD

The present invention relates to micro-chamber plate, and particularly to an analytic micro-chamber plate in which multiple reaction solutions containing a primer or a probe selectively reacted with each nucleic acid are reacted without cross contamination in order to analyze a biological sample solution containing multiple nucleic acids, thereby measuring and analyzing a fluorescence value in real time.

Further, the present invention related to a method of manufacturing the analytic micro-chamber plate.

Further, the present invention relates to a method of manufacturing a micro-chamber plate with a built-in sample, which is used in the manufacturing of the analytic micro-chamber plate.

Further, the present invention relates to an apparatus set for manufacturing the sample containing micro-chamber plate.

BACKGROUND ART

Generally, a micro-chamber is a container which is formed of silicon wafer, glass, metal, plastic or the like and in which a fine reaction less than a few micro-liters. The micro-chamber plate is a plate in which the micro-chambers are arranged in two dimensions and of which one side surface is formed to be sealed after a sample is injected therethrough. Meanwhile, there has been developed a real-time PCR (Polymerase Chain Reaction) method which can measure a fluorescence value increasing in proportion to an amount of genes in real-time, while performing a PCR.

In the real-time PCR method, while the PCR is carried out, the fluorescence value generated from a product of the PCR is measured in every cycle, and the cycle when the fluorescence value larger than a desired value is generated is checked, thereby quantitatively analyzing an initial concentration of a specific gene in a sample.

In the real-time PCR method, there are some advantages in that an electrophoresis process following the PCR is not needed, and it is possible to decide a concentration of a gene having a specific base sequence in the range of $10^9$ or more ("A-Z of Quantitative PCR" edited by Stephen A. Bustin 2004-2006 International University, "Real-time PCR" edited by M. Tevfik Dorak 2006 Taylor & Francis Group).

There had been proposed various kinds of real-time PCR apparatuses for performing the real-time PCR method. For example, there is a conventional real-time PCR apparatus which can analyze 96 or 384 genes using a standard 96-well or 394-well plate, thereby analyzing a plurality of samples (Light cycler 480 manufactured by Roche, ABI 7500, 7900).

In the conventional real-time PCR apparatus manufactured by Roche, in which a reaction sample of 10~50 μl is used, however, there is a problem that it is not possible to analyze a large number of genes compared to a large amount of used sample.

In order to solve the problem, various methods which can simultaneously analyze multiple samples in a shorter time by reducing a used amount of the reaction sample using a MEMS (Micro Electro Mechanical Systems) technology have been proposed, and thus a method using a micro-chamber array plate has been also proposed.

The method using a micro-chamber array plate includes a step of injecting a reaction solution into a micro-chamber, a step of sealing the reaction solution in each micro-chamber, and a reacting and analyzing step. In a method of separately applying a sample solution in each micro-chamber, a transparent micro-chamber plate for cell culture is covered by a semi-permeable membrane so as to individually isolate the micro-chambers, and one cell is cultivated in each micro-chamber, and a Taqman reaction solution is supplied after removing a culture medium, and the micro-chamber is sealed by transparent oil, and then a fluorescence value is measured at a bottom surface of the plate (YASUDA, Kenji EP 1,541, 678 A1, JP 2002245900 NUCLEIC ACID ANALYSIS CHIP AND NUCLEIC ACID ANALYZER).

In the above-mentioned method, however, since different solutions have to be applied to each micro-chamber using a pipette, much time is spent on that. Particularly, an auto-pipetting system is needed in order to inject the sample in 1,536 or more micro-chambers. Herein, in order to apply the different solutions, it takes lots of time due to a cleaning process which has to be performed before applying each of the different solutions. Thus, there is a problem in that it is difficult to use the 384 plates or more.

Secondly, in order to solve the problem, there had been proposed a reactor by E. Tamiya, Hidenori Nagai et al., in which a micro-chamber is formed by treating a silicon wafer in a photolithography process and a chemical etching process (Anal. Chem. 2001 73, 1043-1047, Development of a Micro-chamber Array for Picoliter PCR).

In the reactor, a micro-slide cover glass is used to prevent the evaporation of a PCR solution. However, since cross contamination of the PCR solution is occurred when covering or separating the cover glass, it is inconvenient that the cover glass has to be removed while a water-repellent film is interposed between the cover glass and the wafer, the water-repellent film has to be removed after drying the PCR solution and then an analysis process has to be performed. Further, there is a problem in that it cannot be used in qPCR technology.

Thirdly, in order to solve the problem of using in the qPCR technology, there had been developed another micro-chamber array by Y. Matsubara et al. belonging to the same laboratory, in which a primer is applied to a micro-chamber formed on a wafer using a micro-array device and then dried (7th International Conference on Miniaturized Chemical and Biochemical Analysis Systems Oct. 5-9, 2003, Squaw Valley Calif. USA).

The micro-chamber array uses a method in which mineral oil is applied on a chip so as to completely cover the micro-chambers, and then a PCR solution is dripped on the mineral oil of the reactor using a nano jet pipetting system.

In the method, 1,248 micro-chamber array chips having a volume of 50 nano-liters (0.65×0.65×0.2 mm) are manufactured by treating a 1 inch×3 inch silicon wafer in a photolithography process and a chemical etching process, a primer and a Taqman probe solution are dripped in the micro-chambers using the nano jet pipetting system and dried, and then the mineral oil is coated thereon so that each micro-chamber is isolated and sealed.

In case of the micro-chamber array manufactured by the third method, since a mixed solution of a Taq DNA polymerase and a sample DNA is injected on the mineral oil using the nano jet pipetting system so as to be dripped in each micro-chamber, there is an advantage in that it is possible to successfully carry out the PCR in the micro-chambers without cross contamination of each reaction component.

However, in this method, there are some problems that a separate nano jet pipetting system for micro-array is needed to inject the solution, it takes lots of time to perform the pipetting operation and there is also a high risk of the cross contamination among the reaction solutions due to flowing of the mineral oil when the plate is moved. Further, in a temperature cycling reaction, bubbles are generated at high temperature. Meanwhile, the aqueous solution in each micro-chamber is formed into a globular shape due to a hydrophobic effect between the oil and the aqueous solution, thereby causing a lens effect. Thus since excitation light and luminescence is scattered and dispersed upon the optical measurement, the measurement error is increased.

Fourthly, there had been also developed a picotiter plate in which micro-chambers are formed by the photolithography process and the chemical etching process like in the third method but a lot more reactions than in the third method can be performed (John H. Leamon et al., A massively parallel PocoTiterPlate based platform for discrete pico-liter-scale polymerase chanin reactions, Electrophoresis 2003, 24, 3769-3777).

In the fourth method, it is possible to independently carry out 300,000 PCRs with an amount of 39.5 pl. However, since a carrier in which primers/probes are immobilized is needed, it cannot be applied to a real-time quantitative PCR method in which uniform optical characteristics are required.

Fifthly, in U.S. Pat. No. 5,948,637, there has been proposed a reactor called "a film reactor (or a DNA card)" for reacting a small amount of sample.

The film reactor is form of a three-layered very thin film. Detailedly, a lower film forms a lower surface of the reactor, a middle film forms a side surface of the reactor and an upper film forms an injection hole. After a small amount of sample solution is injected into the film reactor by using a pipette, the injection hole has to be completely sealed. If the injection hole is not completely sealed, there is a problem that the reaction solution is evaporated upon the PCR. Further, since the film reactor has a complicated structure in order to treat a few thousands of samples, it is substantially impossible to manufacture it. Sixthly, in WO 02/40158 and U.S. Pat. No. 6,232,114, there is disclosed a reaction plate which can carry out 1,535 fluorescence analysis reactions with a standard ELISA plate scale.

In the sixth method, multiple through-holes are formed in the plate, and a transparent film having a small fluorescence amount is fused so as to form a plurality of reaction vessels. After the sample is received in each reaction vessel, the reaction vessels are sealed with the transparent film and the reaction is carried out. Upper and lower surfaces of the reaction plate are formed to be transparent, and excitation light is applied through one side surface, and then the fluorescence is measured through the other side surface.

In the sixth method, however, different primer and probe have to be respectively injected into each micro-chamber in order to analyze a great number of genes. In case of a plate for analyzing a great number of samples, since a few thousands of different solutions are injected at the micro-chambers, a special pipetting system such as a nano-liter pipetting system is needed, much time is spent on that and also erroneous injections may be occurred. Further, since the micro-chamber cannot be completely filled with the solution, bubbles are generated, and the water vapors are formed at an upper portion of the micro-chamber when raising the temperature, and thus the optical measurement is disturbed by the scattering.

Seventhly, in PCT/KR2008/005635 invented by the invention of the present application, there is disclosed a reaction plate using a micro-chamber plate that a porous membrane for injecting a sample is formed at one side surface thereof and an optical measuring part is formed at the other side surface thereof.

In the seventh method, multiple through-holes are formed in the plate, and a transparent film having a small fluorescence amount is fused at one side surface thereof so as to form a plurality of reaction vessels. After the sample is received in each reaction vessel, the other side surface thereof is sealed with the porous membrane through which the sample solution can be injected, and the reaction is carried out. In the reaction plate, the sample solution is injected through the porous membrane, and mineral oil is sealingly dripped on the injection surface, and then excitation light is applied and the fluorescence is measured through the optical measuring part formed at the other side surface thereof.

However, in the seventh method, since the injection part and the optical measuring part are formed separately, it has a complicated structure. And the oil layer formed on the injection part becomes transparent, and thus a deviation problem in the measurement results may be occurred according to a stained state of a bottom surface. Further, the injection part on which the mineral oil is dripped may be directed downward in order to perform the reaction and measurement. At this time, the mineral oil having a relatively lower density than the sample may be introduced into the micro-chamber, and thus the scattering may be occurred.

Eighthly, in PCT/KR2008/005635, there is disclosed "The micro-chamber plate, manufacturing method thereof".

However, since the eighth method has a structure that a sample to be injected is directly applied to a porous membrane, it has some problems as follows: 1) in case that the injection of the sample is achieved by a vacuum, centrifugal force is applied in order to prevent running-out of the sample while the vacuum is applied. Herein, discharging of gas through pores of the porous membrane is disturbed by the centrifugal force and surface tension of the sample; 2) since the gas in the micro-chamber is compressed by the centrifugal force and thus a volume thereof is contracted, the gas does not obtain enough buoyancy to get out of the micro-chamber through the membrane, but is remained in the form of small bubbles and then expanded again in the measurement condition of atmospheric pressure, thereby disturbing the measurement.

Therefore, a new micro-chamber plate is needed, in which the sample can be easily injected into the plurality of micro-chambers, the cross-contamination is not occurred, light generated from the sample can be precisely measured in real time without possibility that the optical measuring part is contaminated with the sample or the like.

DISCLOSURE

Technical Problem

An object of the present invention is to provide a micro-chamber plate and a manufacturing method thereof, in which it is prevented that a solution is evaporated in a plurality of micro-chambers needed in a real-time PCR, a fixed temperature enzyme reaction and an LCR (Ligase Chain Reaction), it is possible to facilely inject the solution and thus remarkably reduce time required in an injection process, it is prevented that the solutions in the micro-chambers are mixed with each other, the injection part and the optical measuring part are integrally formed so as to provide a simple structure, such that fine bubbles are not generated, and thus it is possible to more precisely measure the fluorescence value, thereby increasing analyzing accuracy.

Technical Solution

To achieve the object of the present invention, the present invention provides a method of manufacturing a micro-chamber plate with a built-in sample, comprising a step S20 of settling a micro-chamber plate 100 for sample injection at a micro-chamber plate receiving part 200 formed with an upper opening; a step S30 of disposing a cover 310 for micro-chamber plate receiving part so as to cover the upper opening of the micro-chamber plate receiving part 200, the cover 310 for micro-chamber plate receiving part comprising a provisional storing part 312 and an auxiliary covering part 314 connected with the provisional storing part 312 and formed with a through-hole 314-1 for auxiliary covering part; and a step S40 of manufacturing a micro-chamber plate 100A with a built-in sample by putting the micro-chamber plate receiving part 200, on which the cover 310 for micro-chamber plate receiving part is disposed, into a centrifugal separator which can apply vacuum, applying centrifugal force and injecting a sample solution provisionally stored in the provisional storing part 312 into the micro-chamber plate 100 for sample injection through a vessel communication part which is formed at the provisional storing part 312 so as to be communicated with the micro-chamber plate receiving part 200.

Further, the present invention provides a method of manufacturing a micro-chamber plate with a built-in sample, comprising a step S200 of forming a sample solution storing space between a cover 1310 for micro-chamber plate receiving part and an upper surface of a micro-chamber plate 100 for sample injection by closely contacting a lower end of a cover 1310 for micro-chamber plate receiving part to the upper surface of the micro-chamber plate 100 for sample injection, the cover 1310 for micro-chamber plate receiving part comprising a provisional storing part 1312 and an auxiliary covering part 1314 connected with the provisional storing part 1312 and formed with a through-hole 1314-1 for auxiliary covering part; and a step S300 of manufacturing a micro-chamber plate with a built-in sample by putting the micro-chamber plate 100 for sample injection and the cover 1310 for micro-chamber plate receiving part, which are closely contacted with each other so as to form the sample solution space therebetween, into a centrifugal separator which can apply vacuum, applying centrifugal force and injecting a sample solution provisionally stored in the provisional storing part 1312 into the micro-chamber plate 100 for sample injection through a vessel communication part which is formed at the provisional storing part 1312 so as to be communicated with the sample solution storing space.

Preferably, the step S40, S300 of manufacturing the micro-chamber plate 100A with the built-in sample comprises a vacuum and centrifugal force applying step of applying a vacuum into the centrifugal separator and generating first centrifugal force while the vacuum is applied into the centrifugal separator; and a vacuum releasing and centrifugal force applying step of injecting the sample solution into the micro-chamber plate 100 for sample injection by releasing the vacuum in the centrifugal separation while second centrifugal force larger than the first centrifugal force is generated by the centrifugal separator, wherein the first centrifugal force is a centrifugal force which can suppress bumping of the sample solution, while the vacuum is applied into the centrifugal separator, and the vessel communication part is a cutting line 312-1, 1312-1 which is formed at the provisional storing part 312, 1312 so as to be opened by external force, and the second centrifugal force is a centrifugal force which can open the cutting line 312-1, 1312-1.

Further, the present invention provides a method of manufacturing an analytic micro-chamber plate using the micro-chamber plate with the built-in sample manufactured by the above-mentioned method, comprising a step S50 of manufacturing the analytic micro-chamber plate by taking out the micro-chamber plate 100A with the built-in sample from the centrifugal separator and then sealing a separation membrane 130 of the micro-chamber plate 100A with the built-in sample.

Further, the present invention provides an analytic micro-chamber plate in which a body sealing part 120 is formed at a lower surface thereof, a sealed separation membrane is formed at an upper surface thereof, and the unit number of chamber holes 112, which a sample solution including nucleic acid and a special component 140 for analyzing the nucleic acid are built in, is formed, wherein the body sealing part 120 is formed of a material that reflects light, and the sealed separation membrane is a separation membrane 130 which is formed of a porous material and coated and sealed with polymer oil so that a surface of the separation membrane 130 has an increased optical transparency.

Further, the present invention provides an apparatus set for manufacturing a micro-chamber plate with a built-in sample, comprising a micro-chamber plate receiving part 200 which is formed with an upper opening; and a cover 310 for a micro-chamber plate receiving part, which comprises a provisional storing part 312 and an auxiliary covering part 314 connected with the provisional storing part 312 and formed with a through-hole 314-1 for auxiliary covering part, and which covers an upper opening of the micro-chamber plate receiving part 200, the provisional storing part 312 being formed with a vessel communication part which can be opened and closed and is communicated with the micro-chamber plate receiving part 200 when being opened.

Preferably, the apparatus set further comprises a cover 320 for provisional storing part which exposes the through-hole 314-1 for auxiliary covering part to an outside and partially closes the provisional storing part 312, and a lower surface of the provisional storing part 312 is inserted into the micro-chamber plate receiving part 200, and an upper end of the provisional storing part 312 and the auxiliary covering part 314 are disposed at an upper end of the micro-chamber plate receiving part 200, and also the apparatus set further comprises a cover 320 for provisional storing part which covers an upper end of the through-hole 314-1 for auxiliary covering part and an upper end of the provisional storing part 312, wherein the cover 320 for provisional storing part is a membrane filter which allows penetration of gas and prevents penetration of the sample solution, and the vessel communication part is a cutting line 312-1 which is opened by external force.

Further, the present invention provides an apparatus set for manufacturing a micro-chamber plate with a built-in sample, comprising a cover 1310 for micro-chamber plate receiving part, which comprises a provisional storing part 1312 and an auxiliary covering part 1314 connected with the provisional storing part 1312 and formed with a through-hole 1314-1 for auxiliary covering part, and of which a lower end is closely contacted with an upper surface of a micro-chamber plate 100 for sample injection by coupling means so that a sample solution storing space S is formed between the cover 1310 for micro-chamber plate receiving part and the upper surface of the micro-chamber plate 100 for sample injection, wherein the provisional storing part 1312 is formed with a vessel communication part which can be opened and closed and is communicated with the sample solution storing space when being opened.

Preferably, the coupling means comprises a micro-chamber plate receiving part 1200 in which the micro-chamber plate 100 for sample injection is settled; and a coupling case 1400 of which an upper surface is formed with the through-hole 1314-1 for auxiliary covering part and a through-hole 1424 for case communicating the provisional storing part 1312 to an outside, and which compresses an upper end of the cover 1310 for micro-chamber plate receiving part so as to be coupled to the micro-chamber plate receiving part 1200, and the vessel communication part is a cutting line 1312-1 which is opened by external force, and a case cover 1500 is attached to the coupling case 1400 so as to cover the through-hole 1424 for case, such that the through-hole 1314-1 is exposed to an outside and the provisional storing part is closed partially, and the case cover 1500 is attached to the coupling case 1400 so as to cover the through-hole 1424, and the case cover 1500 is a membrane filter which allows penetration of gas and prevents penetration of the sample solution.

Advantageous Effects

According to the present invention as described above, since the separation membrane which is the injection part of the sample solution including nucleic acid is used as the optical measuring part, it is possible to provide a simple structure, prevent measurement error of the optical measuring part due to the contamination, reduce a size of the analytic micro-chamber plate, facilely control the temperature and thus remarkably reduce the analyzing time.

Further, in case that the sample solution including nucleic acid is injected into the chamber hole, since the gas in the chamber hole is firstly removed by using vacuum, and then the injection of the sample solution is performed through the separation membrane, it is possible to completely inject the sample solution within a short time without any remained gas and prevent the error of the optically measured value due to the remain gas.

Further since the separation membrane is sealed with the polymer oil such as mineral oil and silicon oil, it is possible to prevent the cross contamination due to the mixing of the solutions in the chamber holes, thereby increasing the analyzing accuracy.

Further, since the multiple analytic micro-chamber plates can be formed integrally, it is possible to compare and analyze various kinds of samples at the same time, thereby remarkably reducing the analyzing time.

Further, since the separation membrane and the other surface of the optical measuring part can be integrally formed with the analytic micro-chamber plate, the analytic micro-chamber plate of the present invention can be manufactured by the compression molding of aluminum or the like, and thus the production process and manufacturing cost can be remarkably reduced.

DESCRIPTION OF DRAWINGS

The above and other objects, features and advantages of the present invention will become apparent from the following description of preferred embodiments given in conjunction with the accompanying drawings, in which.

---

[Detailed Description of Main Elements]

Figure 1:
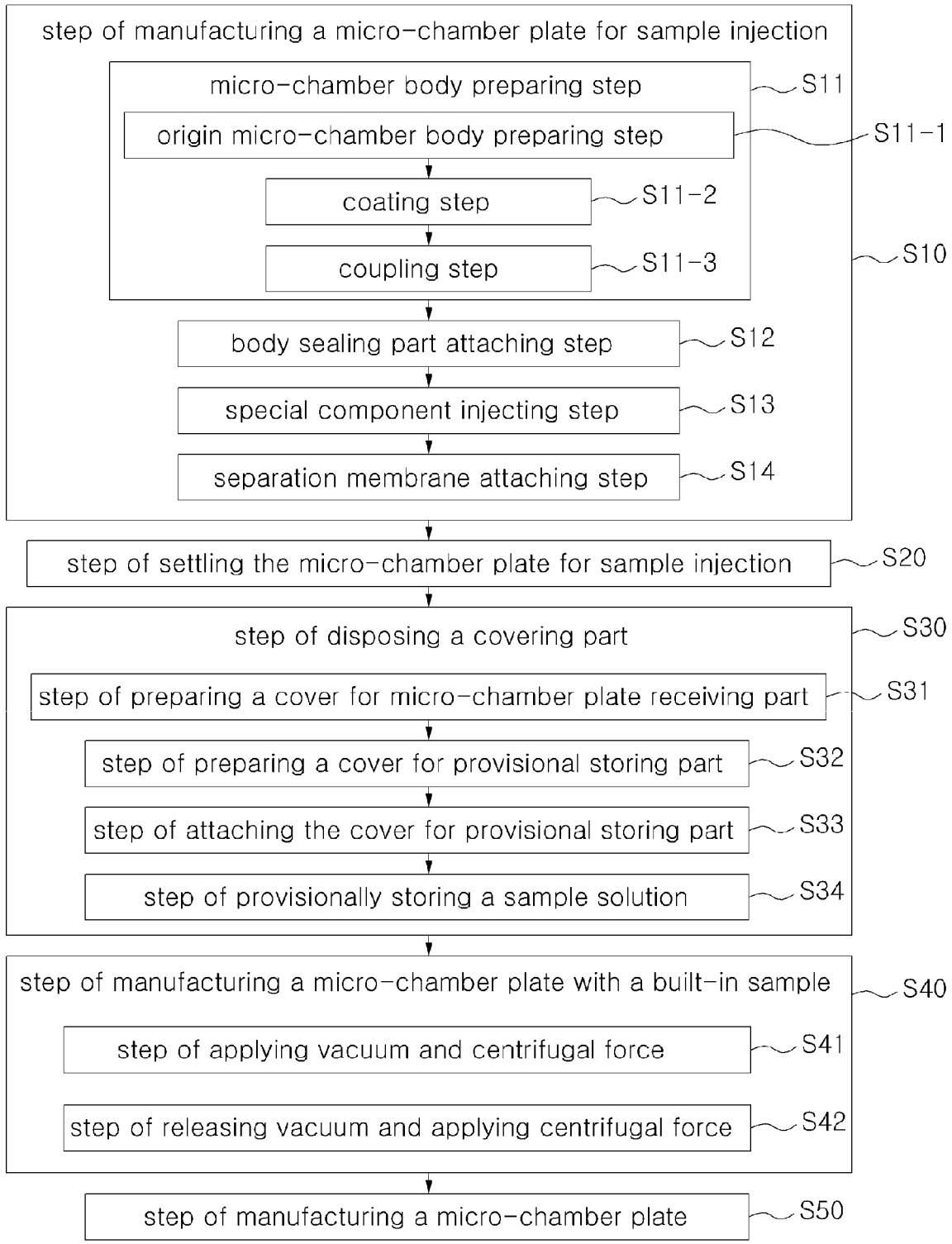
FIG. 1 is a flow chart of a first embodiment of the present invention.

100: micro-chamber plate for sample injection
100A: micro-chamber plate with a built-in sample
112: chamber hole
130: a separation membrane
120: body sealing part
140: special component -continued

[Detailed Description of Main Elements]

200: micro-chamber plate receiving part
300: covering part
310: a cover for micro-chamber plate receiving part
312: provisional storing part
312-1: cutting line
314: auxiliary covering part
314-1: through-hole for auxiliary covering part
320: a cover for provisional storing part
1200: micro-chamber plate receiving part
1310: a cover for micro-chamber plate receiving part
1312: provisional storing part
1312-1: cutting line
1314: auxiliary covering part
1314-1: through-hole for auxiliary covering part
1400: coupling case
1424: through-hole of the case
1500: case cover
S: sample solution storing space

BEST MODE

Hereinafter, the embodiments of the present invention will be described in detail with reference to accompanying drawings.

First Embodiment

The first embodiment relates to a method of manufacturing an analytic micro-chamber plate according to the present invention.

Referring to FIG. 1, the first embodiment includes a step S10 of manufacturing a micro-chamber plate for sample injection, a step S20 of settling the micro-chamber plate for sample injection, a step S30 of disposing a covering part, a step S40 of manufacturing a micro-chamber plate with a built-in sample, and a step S50 of manufacturing an analytic micro-chamber plate.

1. Step S10 of Manufacturing the Micro-Chamber Plate for Sample Injection

Figure 2:
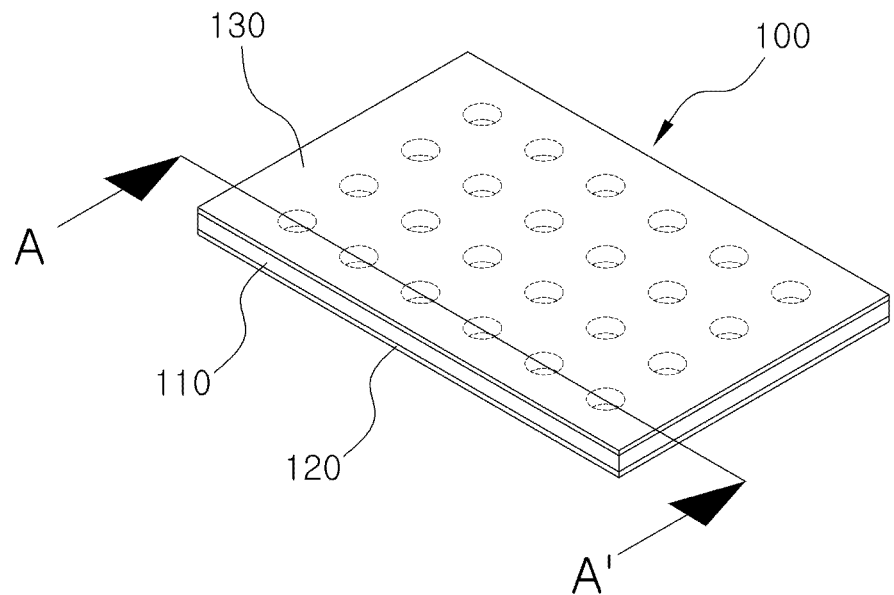
FIG. 2 is a perspective view of a micro-chamber plate for sample injection, which is prepared by a manufacturing step of the micro-chamber plate for sample injection in FIG. 1.
Figure 3:
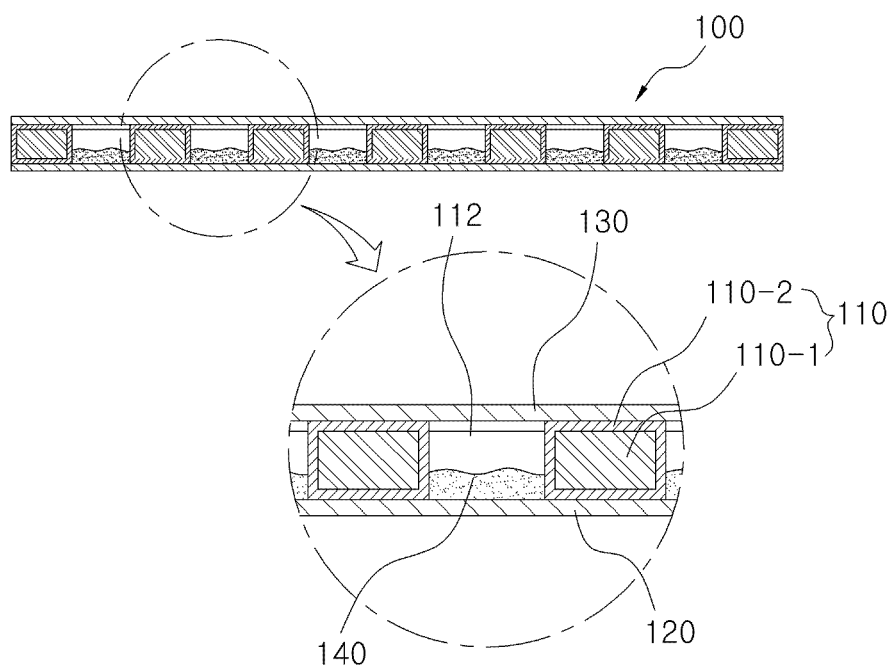
FIG. 3 is a cross-sectional view taken along a line A-A' of FIG. 2.
Figure 4:
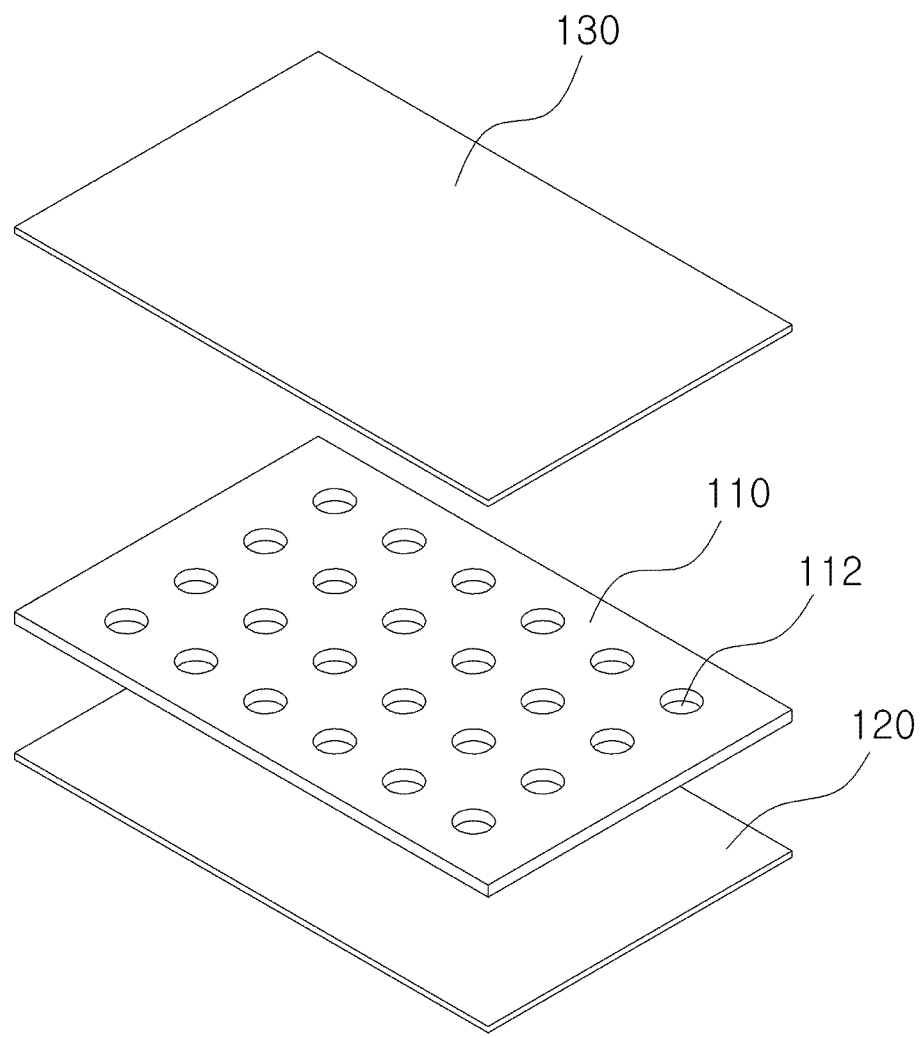
FIG. 4 is an exploded perspective view of a main part in FIG. 2.

Referring to FIGS. 2 to 4, in the step S10 of manufacturing the micro-chamber plate for sample injection, the micro-chamber plate 100 for sample injection, in which a special component 140 is built in, is manufactured. The micro-chamber plate 100 for sample injection includes a micro-chamber body 110, a body sealing part 120 and a separation membrane 130.

Therefore, referring to FIGS. 1 to 4, the step S10 of manufacturing the micro-chamber plate for sample injection includes a micro-chamber body preparing step S11 which prepares the micro-chamber body 110, a body sealing part attaching step S12 which forms the body sealing part 120 at a lower surface of the micro-chamber body 110, a special component injecting step S13 which injects the special component 140, and a separation membrane attaching step S14 which forms the separation membrane 130 at an upper surface of the micro-chamber body 110.

Meanwhile, referring to FIG. 1, the micro-chamber body preparing step S11 includes a origin micro-chamber body preparing step S11-1, a coating step S11-2 and a coupling step S11-3.

Figure 5:
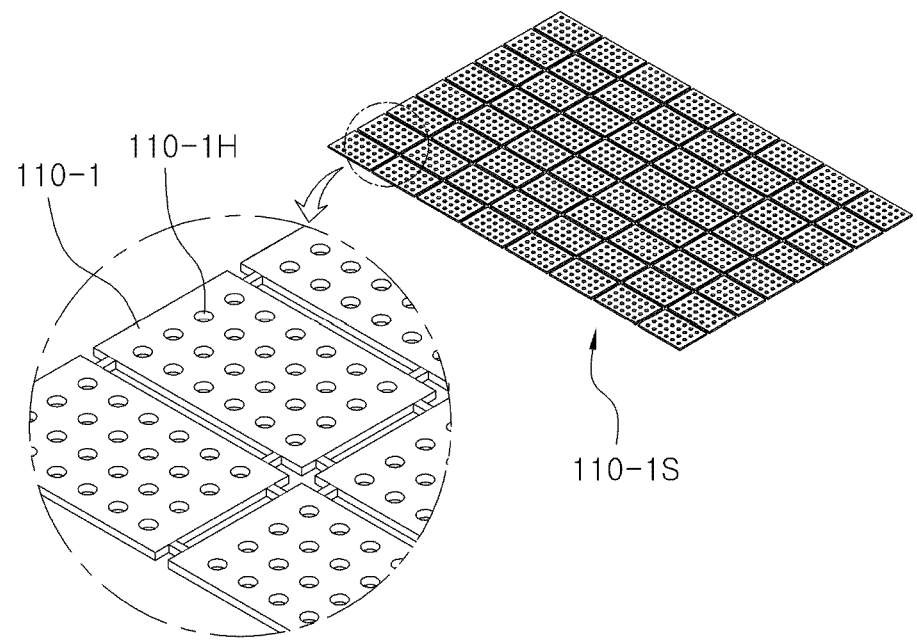
FIG. 5 is a perspective view of an origin micro-chamber body prepared in a manufacturing step of the origin micro-chamber body in FIG. 1.
Figure 6:
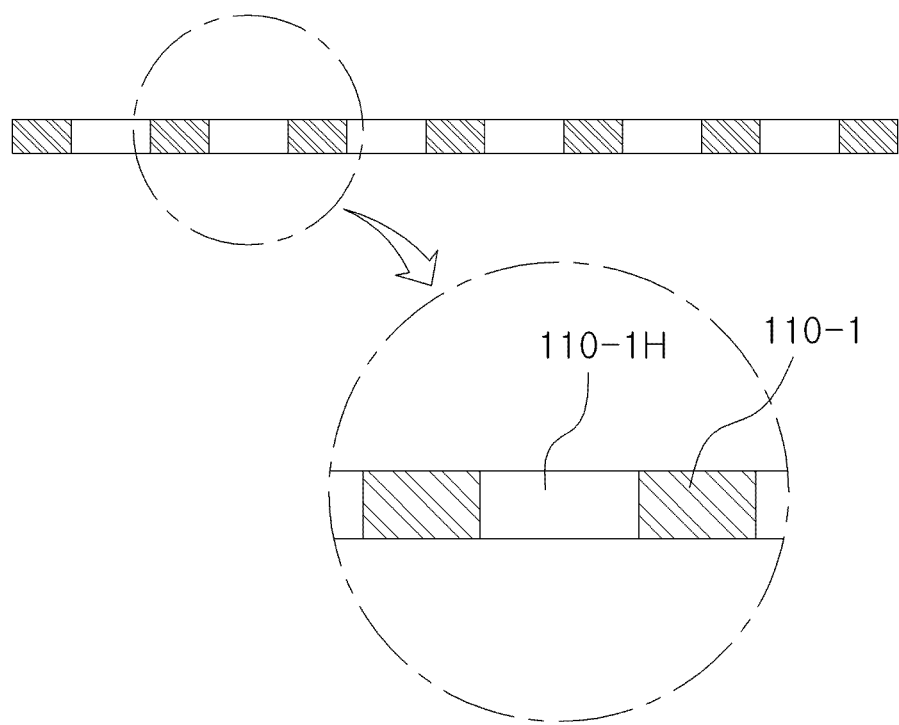
FIG. 6 is a cross-sectional view of the origin micro-chamber body in FIG. 5.

Referring to FIGS. 5 and 6, in the origin micro-chamber body preparing step S11-1, an origin micro-chamber body 110-1 which is formed with a unit number of origin chamber holes 110-1H passing through upper and lower surfaces thereof is prepared. The origin micro-chamber body 110-1 is formed of a material, preferably, which has durability against heat applied in a polymerase chain reaction (PCR) or other analyzing reaction, more preferably, which is not deformed at 0~100° C. Therefore, the origin micro-chamber body 110-1 may be formed of an aluminum, silicon wafer, glass, metallic or plastic material. Meanwhile, a plurality of the origin micro-chamber bodies 110-1 may be connected with each other through connecting pieces (not designated by a reference numeral). A reference numeral 110-1S is an origin micro-chamber body set formed by connecting the multiple origin micro-chamber bodies 110-1.

Figure 7:
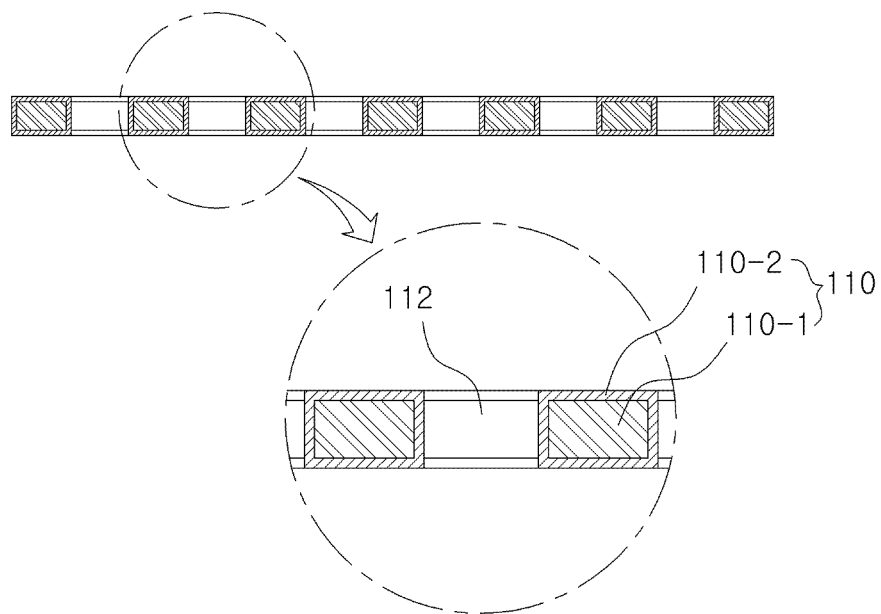
FIG. 7 is a cross-sectional view of explaining a coating step and a coupling step in FIG. 1.

Referring to FIG. 7, the micro-chamber body 110 is manufactured through the coating step S11-2 and the coupling step S11-3. In the micro-chamber body 110, the unit number of chamber holes 112 corresponding to the unit number of origin chamber holes 110-1H are formed. Each chamber hole 110-1H may be formed to have a width of 0.3 to 3 mm and a depth of 0.5 to 5 mm. In case of the first embodiment, since multiple chamber holes 112 are formed in one micro-chamber body 110, it is possible to quantitatively analyze a large number of nucleic acids at the same time, and since the chamber hole 112 has a shallow depth, it is possible to provide high thermal conduction performance, reduce an analyzing time and also improve analyzing accuracy.

Referring to FIG. 7, in the coating step S11-2, the origin micro-chamber body 110-1 is dipped in a polymer solution, and thus a polymer coating layer 110-2 is formed on a surface of the origin micro-chamber body 110-1 and inner surfaces of the unit number of origin chamber holes 110-1H (referring to FIG. 6).

In the embodiment, an aqueous solution in which ES-120s (which was copolymer polyester obtained by reacting complex aromatic dicarboxylic acid and complex aliphatic diol) resin, as a polyester-based resin, manufacture by Basekorea co., Ltd. was diluted to 50% with toluene (4) and MEK (1) was diluted to 5~20 vol % using toluene so as to have an adjusted viscosity. Then, the origin micro-chamber body 110-1 was coated while changing the dipping number thereof from one time to three times. In order to prevent clogging of the origin chamber hole 110-1H and also obtain the uniform polymer coating layer 110-2, it was the most preferable that the viscosity was 5 to 10 vol % and the dipping number was two times. Meanwhile, in case that the origin micro-chamber body 110-1 is formed of aluminum, it is preferable that a white anodizing step in which the surface of the origin micro-chamber body 110-1 is white-anodized is carried out before the coating step S11-2.

Referring to FIG. 7, in the coupling step S11-3, a surface of the polymer coating layer 110-2 is treated by a coupling process. The coupling process is to remove carboxylic acid as a functional group which is present in the polyester-based resin.

In the embodiment, the coupling process was carried out under an ethanol solvent using 1-Ethyl-3-[3-dimethylaminopropyl]carbodiimide hydrochloride (EDC) and 4-Dimethylaminopyridine (DMAP). First of all, DMAP and EDC having a concentration of 0.25M were prepared respectively, and 50 ml of DMAP and 9 ml of EDC were mixed and reacted for 12 hours or more at room temperature. And then three times of cleaning processes are performed using ethanol and distilled water, respectively, and the coupling process was completed by desiccation.

Since the polyester-based resin used in the present invention is colorless and transparent and also has very excellent adhesive property with respect to an aluminum surface, it is estimated that the polyester-based resin is the most suitable.

Figure 8:
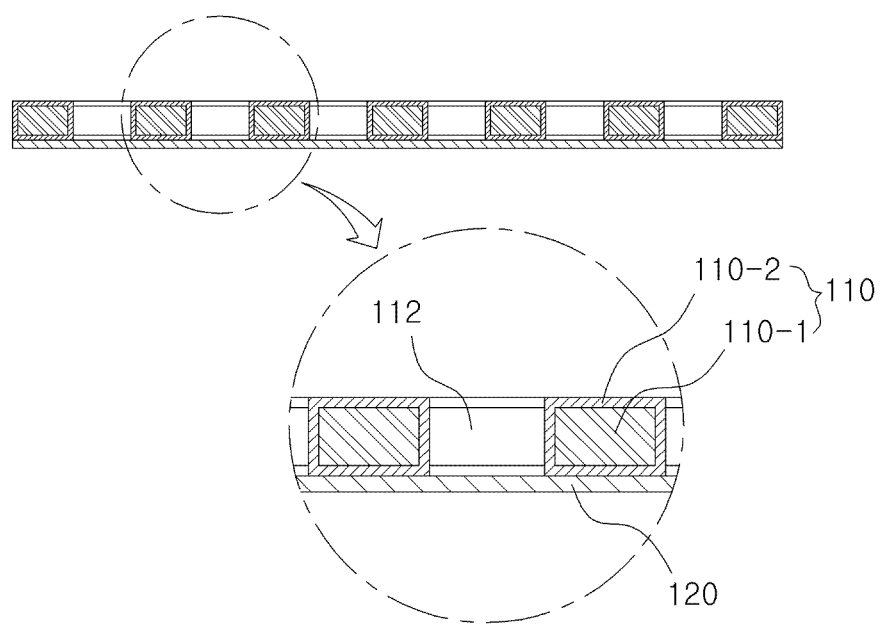
FIG. 8 is a cross-sectional view of explaining a step of attaching a body sealing part in FIG. 1.

Referring to FIG. 8, in the body sealing part attaching step S12, lower openings of the unit number of chamber holes 112 are sealed by the body sealing part 120 after the coupling step S11-3. In the body sealing part attaching step S12, the body sealing part 120 is contacted with the polymer coating layer 110-2 and then pressed at a high temperature so as to be attached to the polymer coating layer 110-2. The body sealing part 120 may be formed of a material, which can reflect light to the separation membrane 130 (referring to FIG. 17), in order to facilely irradiate light through the separation membrane 130 (referring to FIG. 17) upon the optical measurement and then facilely measure excitation light generated from the sample. Therefore, in case that the lower openings of the unit number of chamber holes 112 are sealed with a transparent film, the body sealing part 120 may further include a reflecting film attached to an outer surface of the transparent film. Meanwhile, in case that the body sealing part 120 is formed of other material which is not transparent or does not reflect light, a reflecting layer may be further provided on a surface of the body sealing part 120, which is corresponding to the lower openings of the unit number of chamber holes 112. Meanwhile, the body sealing part 120 is formed of a material which can prevent leakage of a sample solution including nucleic acid.

In the embodiment, a product of a transparent or opaque white polymer film type was used as the body sealing part 120. For example, a transparent film formed of a PET (polyethylene terephthalate) material and having a thickness of 40 μm and an opaque white film (brand name: ST-DF-50W), which were manufacture by KM industrial co., Ltd., were used all. By using these, it was possible to obtain more precise optical measurement values.

Figure 9:
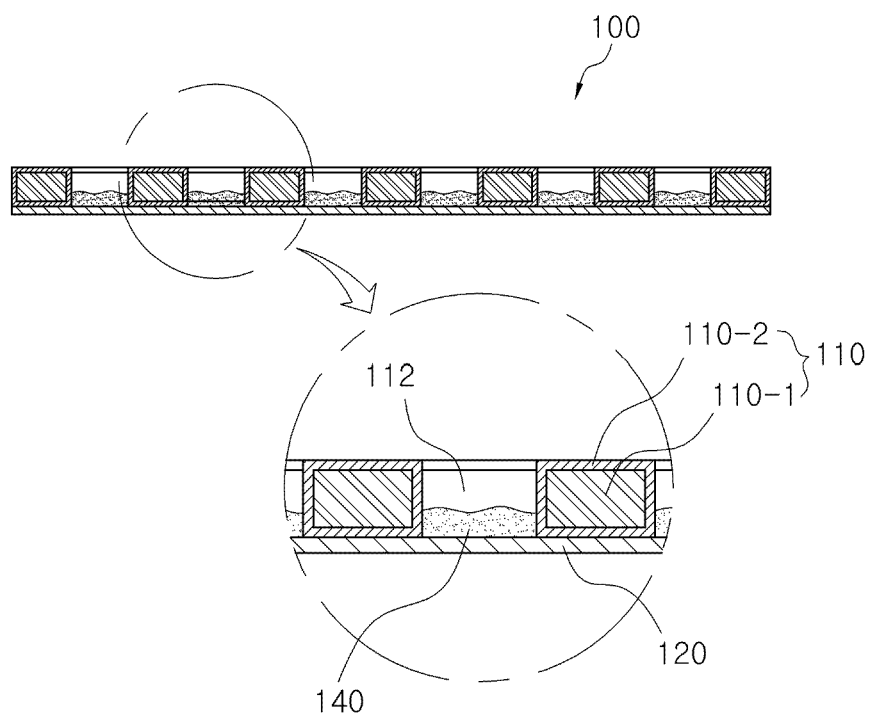
FIG. 9 is a cross-sectional view of explaining a special component injecting step in FIG. 1.

Referring to FIG. 9, in the special component injecting step S13, the special component 140 for analyzing nucleic acid containing a primer or a probe is injected into each of the unit number of chamber holes 112 of which the lower openings are sealed by the body sealing part 120. The special component 140 may further include a fluorescence analyzing agent for analyzing nucleic acid, and if necessary, a nucleic acid amplifying enzyme, dNTP, a buffer or a stabilizer (e.g., polyol, carbohydrate, so albumin or the like which is molecularly mixed well with the reaction solution, primer, enzyme or the like, thereby stabilizing them and reducing attachment to the vessel). The special component 140 may be used in a dried, semi-dried or liquefied state according to its composition.

Referring to FIG. 3, in the separation membrane attaching step S14, the separation membrane 130 is attached to an upper surface of the micro-chamber body 110. That is, in the separation membrane attaching step S14, the separation membrane 130 is attached to upper end sides of the unit number of chamber holes 112 so as to cover upper openings of the unit number of chamber holes 112 in which the special component 140 is injected. The separation membrane 130 is formed so as to prevent penetration of the special component 140 but allow penetration of the sample solution. Therefore, the special component 140 is prevented from being leaked from an inner side of the chamber hole 112 to an outside through the separation membrane 130, but the sample solution including nucleic acid can be introduced from an outside into the chamber hole 112 through the separation membrane 130. Therefore, the separation membrane 130 may be formed of a porous material which prevents the penetration of the special component 140 but allows the penetration of the sample solution including nucleic acid. In case that the separation membrane 130 is formed of a porous material, the separation membrane 130 may be sealingly coated with polymer oil so as to improve an optical transparency of the separation membrane 130, thereby facilitating the optical measurement with respect to the sample in the chamber hole 112. The polymer oil may be mineral oil, silicone oil, hydrocarbon oil, paraffin wax or the like. The separation membrane 130 formed of the porous material may be formed of a micro-pore shape, a mesh shape or an unwoven shape. Preferably, the porous material has a pore size of 0.1 to 100 μm. The porous separation membrane 130 may be a polymer membrane. Meanwhile, the separation membrane 130 is pressed at a high temperature while being contacted with the polymer coating layer 110-2 and thus attached to the polymer coating layer 110-2.

In the embodiment, a great number of porous materials having desired pore sizes were used as the separation membrane 130. More detailedly, a product formed of a PC (polycarbonate) material and having a pore size of 12 μm, which was manufacture Whatman company was used. This was caused by that the sample injection was facile due to its large pore size and the transparency was increased by the mineral oil, thereby facilitating the optical measurement.

Meanwhile, in other embodiment, the separation membrane 130 may be formed of a film which can be punched. This type of separation membrane may be formed of Teflon, polypropylene, polyethylene, polyester or polyvinyl chloride. 1 to 10 hollowed portions may be formed per one chamber hole 112. In order to prevent leakage of the built-in special component 140 and facilitate injection of the sample solution including nucleic acid, the punched portion may have a width of 10 μm to 1 mm or 100 to 500 μm. Meanwhile, since the film type separation membrane has a good optical transparency, it may make the optical measurement possible.

2. Step S20 of Settling the Micro-Chamber Plate for Sample Injection

Figure 10:
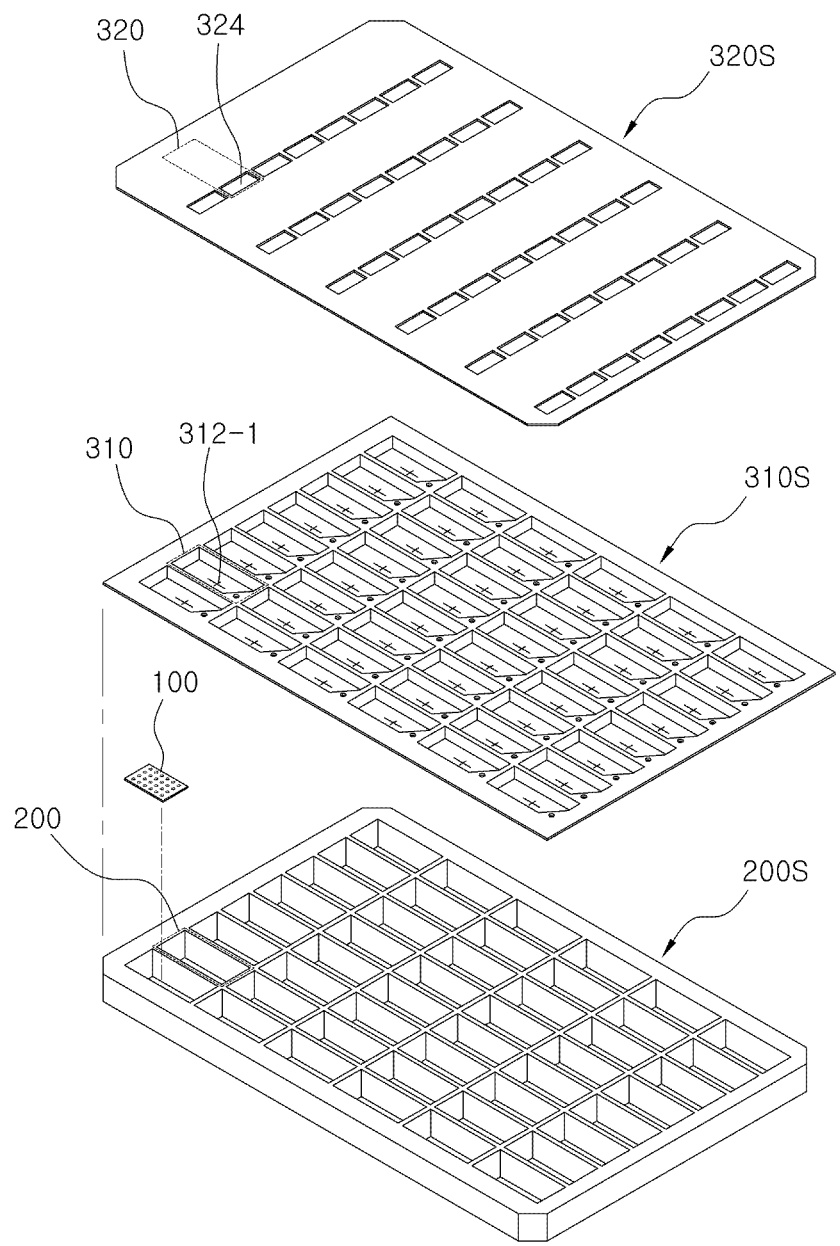
FIG. 10 is an exploded perspective view of explaining a step of settling the micro-chamber plate for sample injection, a step of disposing a covering part and a step of manufacturing a micro-chamber plate with a built-in sample.
Figure 11:
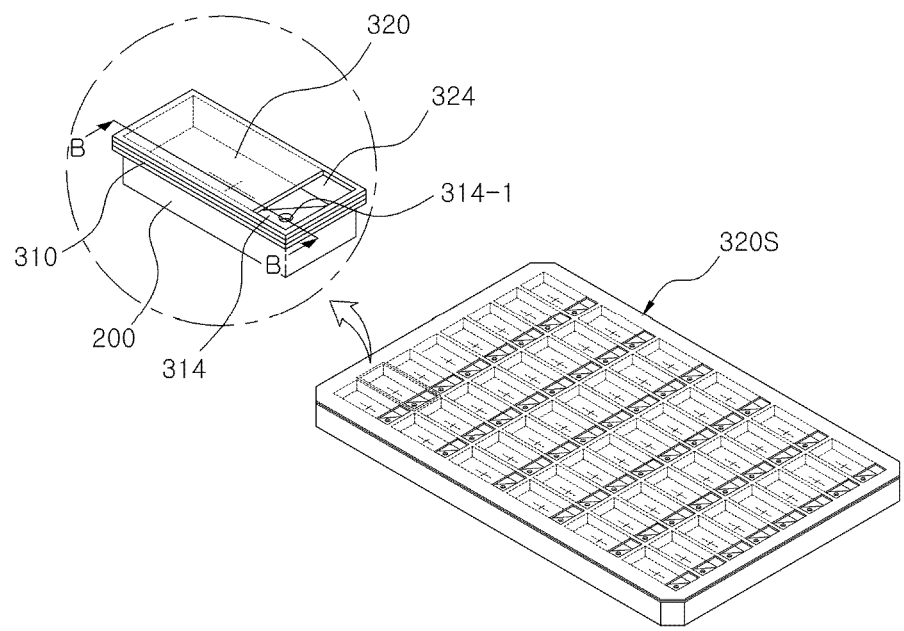
FIG. 11 is an assembled perspective view of FIG. 10.
Figure 12:
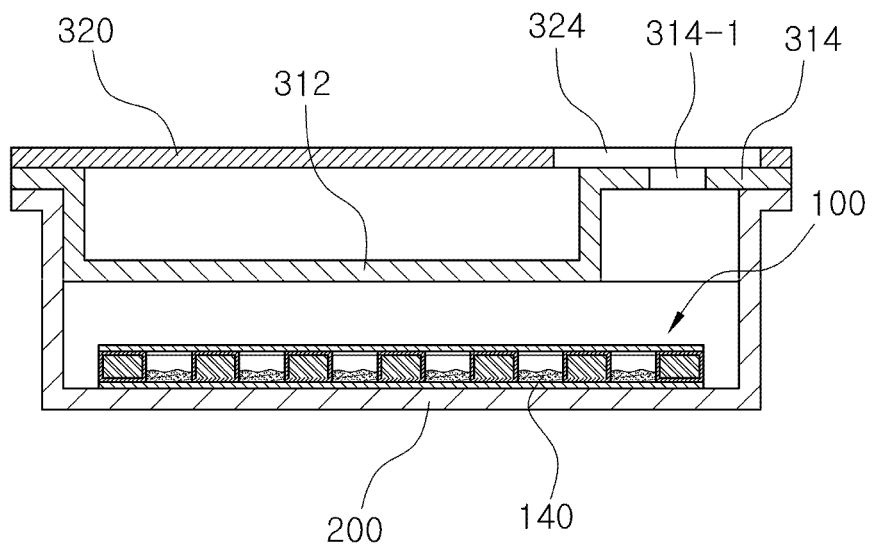
FIG. 12 is a cross-sectional view taken along a line B-B' of FIG. 11, in which the micro-chamber plate for sample injection is settled.

Referring to FIGS. 10 to 12, in the step S20 of settling the micro-chamber plate for sample injection, the micro-chamber plate 100 for sample injection is settled at a micro-chamber plate receiving part 200 formed with an upper opening. A reference numeral 200S is a micro-chamber plate receiving part set in which multiple micro-chamber plate receiving parts 200 are connected with each other.

3. Step S30 of Disposing a Covering Part

Referring to FIG. 1, the step S30 of disposing the covering part includes a step S31 of preparing a cover for micro-chamber plate receiving part, a step S32 of preparing a cover for provisional storing part, a step S33 of attaching the cover for provisional storing part and a step S34 of provisionally storing a sample solution.

Figure 13:
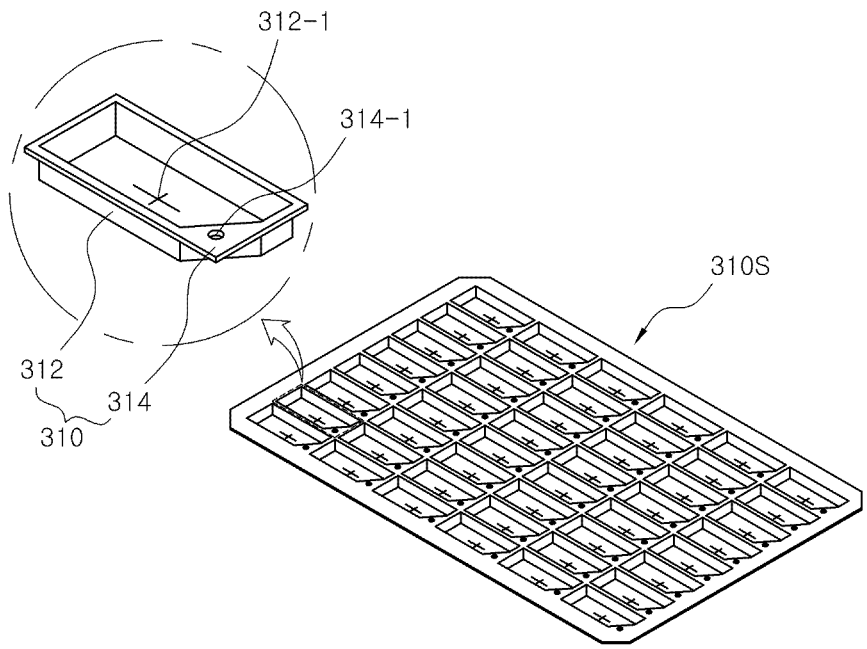
FIG. 13 is an enlarged view of a cover for micro-chamber plate receiving part in FIG. 10.

Referring to FIG. 13, in the step S31 of preparing a cover for micro-chamber plate receiving part, 312, a cover 310 for micro-chamber plate receiving part, in which a provisional storing part 312 and an auxiliary covering part 314 are formed integrally, is prepared. A reference numeral 310S is a cover set for micro-chamber plate receiving part, in which multiple covers 310 for micro-chamber plate receiving part are connected with each other.

Referring to FIG. 13, the provisional storing part 312 is a vessel which provisionally stores the sample solution including nucleic acid, and a vessel communication part is formed at a lower surface thereof. The vessel communication part may be a cutting line 312-1 which is opened by external force. Therefore, if the external force is not applied to the lower surface of the provisional storing portion 312, it is prevented that the sample solution including nucleic acid which is provisionally stored in the provisional storing part 312 is leaked to an outside of the provisional storing part 312. The provisional storing part 312 may be formed of a silicon material. Meanwhile, the cutting line 312 may be in the formed of "+" shape, "<" shape, "=" shape or "×" shape.

Referring to FIG. 13, the auxiliary covering part 314 is formed into a plate shape which is connected to an upper end of a circumferential surface of the provisional storing part 312 so as to be arranged horizontally. The auxiliary covering part 314 is formed with a through-hole 314-1 for auxiliary covering part, which passes through upper and lower surfaces of the auxiliary covering part 314.

Figure 14:
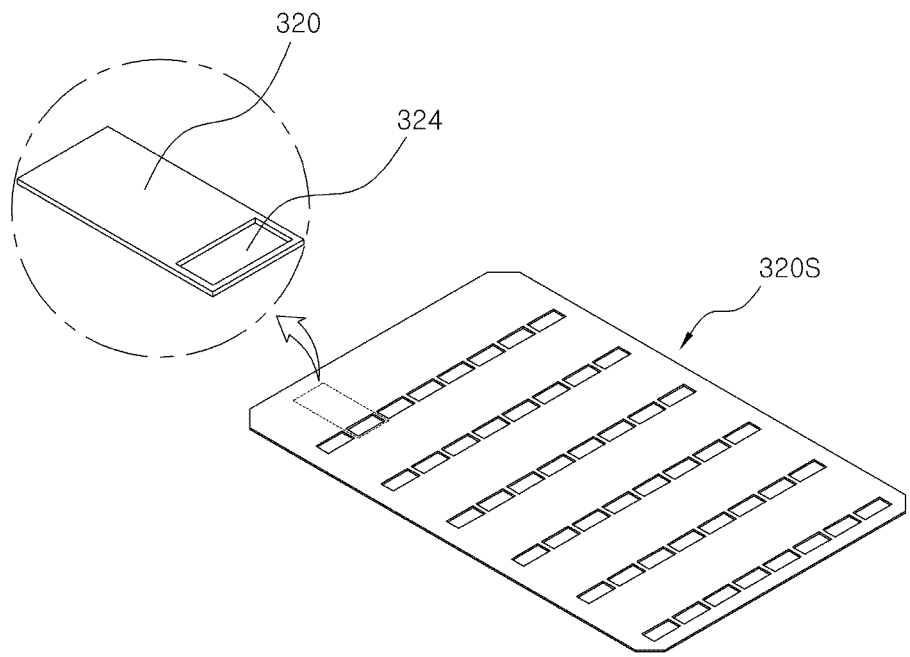
FIG. 14 is an enlarged view of a cover for provisional storing part in FIG. 10.

Referring to FIG. 14, in the step S32 of preparing a cover for provisional storing part, a cover 320 for provisional storing part formed with a through-hole 324 for provisional storing part cover is prepared. The cover 320 for provisional storing part may be formed into a thin film shape. A reference numeral 320S is a cover set for provisional storing part, in which multiple covers 320 for provisional storing part are connected with each other.

Figure 15:
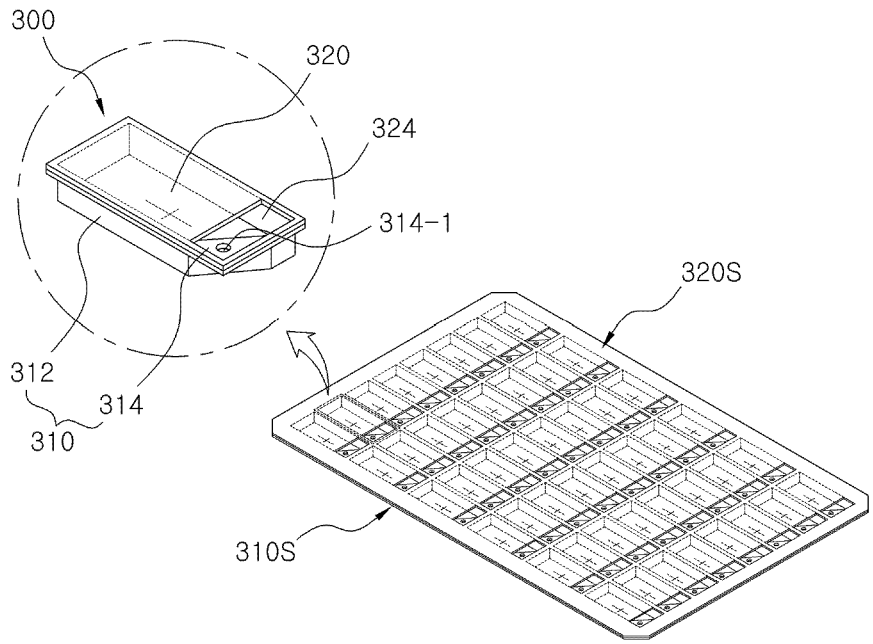
FIG. 15 is a perspective view of the covering part formed by coupling the cover for the micro-chamber plate receiving part and the cover for provisional storing part.

Referring to FIG. 15, the cover 320 for provisional storing part is formed so that the through-hole 314-1 for auxiliary covering part is exposed to an outside and an upper portion of the provisional storing part 312 is partially closed when the cover 320 for provisional storing part is attached to an upper end of the cover 310 for micro-chamber plate receiving part. In this case, the rest of the upper portion of the provisional storing part 312 is exposed to the outside through the through-hole 324 for provisional storing part cover.

Referring to FIG. 15, in the step S33 of attaching the cover for provisional storing part, the cover 320 for provisional storing part is attached to the upper end of the cover 310 for micro-chamber plate receiving part. In order to attach the cover 320 for provisional storing part, an adhesive may be previously applied to the cover 310 for micro-chamber plate receiving part. The adhesive may be a polymer adhesive, a double-sided tape or the like. Therefore, the upper portion of the provisional storing part 312 is closed partially, and the through-hole 314-1 for auxiliary covering part and the rest of the upper portion of the provisional storing part 312 are exposed to the outside through the through-hole 324 for provisional storing part cover. A covering part 300 is formed by performing the step S33 of attaching the cover for provisional storing part.

Figure 16:
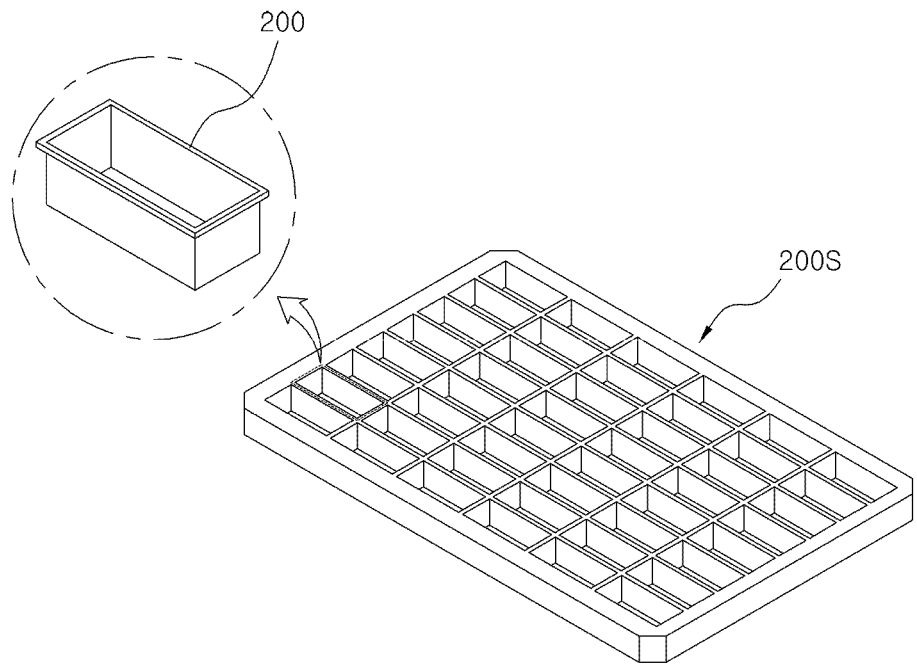
FIG. 16 is an enlarged view of the micro-chamber plate receiving part in FIG. 10.

Referring to FIGS. 11, 15 and 16, if the step S33 of attaching the cover for provisional storing part is carried out, the covering part 300 is settled on an upper end of the micro-chamber plate receiving part 200 while covering an upper opening of the micro-chamber plate receiving part 200.

Referring to FIG. 12, if the covering part 300 is settled on an upper end of the micro-chamber plate receiving part 200, a lower surface of the provisional storing part 312 is inserted into the micro-chamber plate receiving part 200, and an upper end of the provisional storing part 312 and the auxiliary covering part 314 are disposed on an upper end of the micro-chamber plate receiving part 200.

Referring to FIG. 12, if the covering part 300 is settled on the upper end of the micro-chamber plate receiving part 200, an inner side of the micro-chamber plate receiving part 200 is communicated with the outside through the through-hole 314-1 for auxiliary covering part and the through-hole 324 for provisional storing part cover, and the provisional storing part 312 is communicated with the outside through the through-hole 324 for provisional storing part cover.

Referring to FIG. 12, in the step S34 of provisionally storing the sample solution, the sample solution including nucleic acid is provisionally stored in the provisional storing part 312 through the through-hole 324 of provisional storing part cover.

4. Step S40 of Manufacturing a Micro-Chamber Plate with a Built-in Sample

Referring to FIG. 1, the step S40 of manufacturing the micro-chamber plate with the built-in sample includes a step S41 of applying vacuum and centrifugal force and a step S42 of releasing vacuum and applying centrifugal force.

In the step S41 of applying the vacuum and centrifugal force, first of all, the micro-chamber plate receiving part 200 on which the covering part 300 is disposed is put into a centrifugal separator which can apply vacuum. In this case, referring to FIG. 11, the through-hole 324 for provisional storing part cover is directed upward, and the cover 320 for provisional storing part is directed to a rotational center of the centrifugal separator, and the lower surface of the micro-chamber plate receiving part 200 is directed to an opposite side of the rotational center of the centrifugal separator. Then, the vacuum is applied to the centrifugal separator, and the centrifugal separator is operated so that first centrifugal force is applied to the micro-chamber plate receiving part 200. If the centrifugal force is not applied in the vacuum state, a boiling point of the sample solution including nucleic acid is lowered, and bumping phenomenon is occurred, thereby resulting in contamination. Therefore, the first centrifugal force functions to suppress the bumping phenomenon while the vacuum is applied in the centrifugal separator. Further, the cutting line 312-1 is not opened by the first centrifugal force, and thus it is prevented that the cutting line 312-1 is opened by the first centrifugal force and the solution is contacted with the separation membrane 130.

Figure 17:
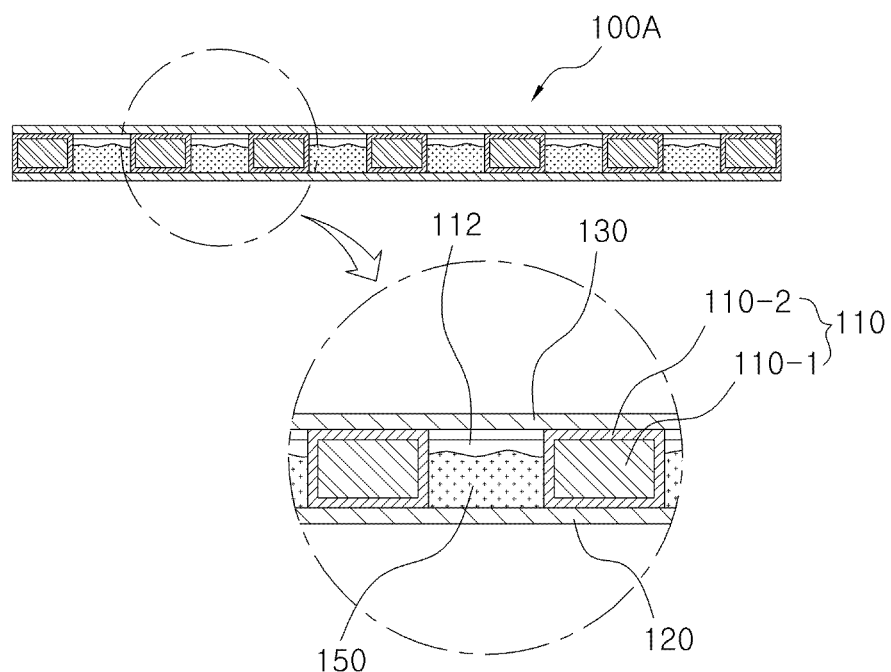
FIG. 17 is a cross-sectional view of the micro-chamber plate with the built-in sample, which is corresponding to FIG. 3.

In the step S42 of releasing the vacuum and applying the centrifugal force, second centrifugal force generated from the centrifugal separator is larger than the first centrifugal force, such that the cutting line 312-1 is opened by the second centrifugal force. Then, the vacuum applied in the centrifugal separator is released, and the sample solution is injected into the micro-chamber plate 100 for sample injection through the cutting line 312-1 and the separation membrane 130. Therefore, as shown in FIG. 17, the sample solution is injected in the chamber hole 112, and thus a micro-chamber plate 100A with a built-in sample which is mixed with the special component 140 (referring to FIG. 3) is prepared. A reference numeral 150 is a mixed solution of the special component 140 (referring to FIG. 3) and the sample solution.

According to the embodiment, in the step S41 of applying the vacuum and centrifugal force, the first centrifugal force is maintained to be less than 42 g, and the bumping of the sample solution is suppressed.

In the step S42 of releasing the vacuum and applying the centrifugal force, the centrifugal force is gradually increased and maintained to be more than 242 g, and the sample solution is injected for 1 minute into the micro-chamber plate 100 for sample injection while the vacuum is released. Therefore, the sample solution can be completely injected into the chamber hole 112.

A reason why the sample solution is injected while the vacuum is released is as follows: if the sample solution is contacted with the separation membrane 130 while the vacuum is applied, it is impossible to completely inject the sample solution due to the property of the separation membrane 130.

5. Step S50 of Manufacturing a Micro-Chamber Plate

In the step S50 of manufacturing a micro-chamber plate, first of all, the micro-chamber plate 100A with the built-in sample (referring to FIG. 17) is taken out of the centrifugal separator. Then, a surface of the separation membrane 130 of the micro-chamber plate 100A with the built-in sample (referring to FIG. 17) is sealed so that the sample solution built in the micro-chamber plate 100A with the built-in sample (referring to FIG. 17) is not leaked to the outside upon an analyzing reaction including the PCR reaction. Further, the sealing of the surface of the separation membrane 130 is performed so that the optical transparency of the separation membrane 130 is increased and thus the optical measurement with respect to the sample in the chamber hole 112 can be facilely performed through the separation membrane 130.

By performing the step S50 of manufacturing a micro-chamber plate, an analytic micro chamber plate which can be used in the analyzing reaction including the PCR is manufactured.

Since the special component 140 including the primer or probe is built in the analytic micro chamber plate, the analytic micro chamber plate can be used in a real-time PCR, and it can be also used in a fixed temperature enzyme reaction and an LCR (Ligase Chain Reaction). Further, it can be used variously by changing the special component 40 or the like.

In case of the first embodiment, since the separation membrane 130 is formed of the porous material, the surface of the separation membrane 130 of the micro-chamber plate 100A with the built-in sample is coated and sealed with the polymer oil. The polymer oil may be mineral oil, silicone oil, hydrocarbon oil, paraffin wax or the like. In case that the separation membrane 130 is a polypropylene membrane, it may be coated and sealed with the mineral oil.

If the separation membrane 130 which is the polypropylene membrane is coated and sealed with the mineral oil, the hydrophobic mineral oil pushes the sample including water penetrated through the hydrophobic polypropylene membrane and then occupies the place due to hydrophilicity-hydrophobicity effect. Meanwhile, since the mineral oil has a density similar to the polypropylene membrane, the optical transparency of the separation membrane 130 is increased and the optical measurement with respect to the sample in the chamber hole 112 is facilitated, and since the polypropylene membrane is sealed with the mineral oil, it is prevented that the sample in the chamber hole 112 is leaked and evaporated.

Meanwhile, in other embodiment, if the separation membrane 130 is formed of the film which can be punched, the surface of the separation membrane 130 of the micro-chamber plate 100A with the built-in sample (referring to FIG. 17) may be sealed with an adhesive film (tape).

Meanwhile, in case of other embodiment, the cover 320 for provisional storing part may be a membrane filter which allows the penetration of gas but prevents the penetration of the sample solution. In order to attach the membrane filter as the cover 320 for provisional storing part, an adhesive may be previously applied to the cover 310 for micro-chamber plate receiving part. The adhesive may be a polymer adhesive, a double-sided tape or the like. In case that the cover 320 for provisional storing part is attached to the upper end of the cover 310 for micro-chamber plate receiving part, the cover 320 for provisional storing part is formed to cover the upper end of the through-hole 314-1 for auxiliary covering part and the upper end of the provisional storing part 312. In this case, the step S34 of provisionally storing the sample solution is carried out before the step S33 of attaching the cover for provisional storing part.

Meanwhile, in case of other embodiment, it may not include the step S32 of preparing a cover for provisional storing part and the step S33 of attaching the cover for provisional storing part. In this case, the covering part 300 may be the cover 310 for micro-chamber plate receiving part. Therefore, before the step S41 of applying the vacuum and centrifugal force, a bottom surface of the provisional storing part 312 is directed downward (not gravity direction) so that the sample solution is not leaked through the opened upper portion of the provisional storing part 312. As the step S41 of applying the vacuum and centrifugal force is carried out, the opened upper portion of the provisional storing part 312 is directed to the rotational center of the centrifugal separator, and the lower surface of the provisional storing part 312, i.e., the cutting line 312-1 is directed to an opposite side of the rotational center of the centrifugal separator.

Meanwhile, in case of other embodiment, the cover 320 for provisional storing part may be formed to cover the through-hole 314-1 for auxiliary covering part and the provisional storing part 312. In this case, the cover 320 for provisional storing part is the membrane filter which allows the penetration of gas but prevents the penetration of the sample solution. In this case, the cover 320 for provisional storing part is not formed with the through-hole 324 for provisional storing part cover.

Second Embodiment

The second embodiment relates to a method of manufacturing the micro-chamber plate with a built-in sample according to the present invention.

The second embodiment includes a step S10 of manufacturing a micro-chamber plate for sample injection, a step S20 of settling a micro-chamber plate for sample injection, a step S30 of disposing a covering part, and a step S40 of manufacturing a micro-chamber plate with the built-in sample which are described in the first embodiment. The description thereof is based on that of the first embodiment.

Third Embodiment

The third embodiment relates to an analytic micro-chamber plate.

The analytic micro-chamber plate (not shown) is the same as the micro-chamber plate 100A with the built-in sample (referring to FIG. 17) except the separation membrane 130, and thus it will be described with reference with FIG. 17.

Referring to FIGS. 6 and 17, the third embodiment includes an origin micro-chamber body 110-1 in which the unit number of chamber holes 110-1H are formed to pass through upper and lower surfaces thereof.

Referring to FIGS. 7 and 17, a polymer coating layer 110-2 is formed on a surface of the origin micro-chamber body 110-1 and inner surfaces of the unit number of origin chamber holes 110-1H (referring to FIG. 6). The unit number of chamber holes 112 corresponding to the unit number of origin chamber holes 110-1H are formed by the polymer coating layer 110-2.

Referring to FIGS. 8 and 17, a body sealing part 120 is formed at a lower surface of the micro-chamber body 110 so as to seal lower openings of the unit number of chamber holes 112. The body sealing part 120 is to prevent leakage of the sample solution including nucleic acid. Meanwhile, the body sealing part 120 is formed of a PET (polyethylene terephthalate) material which reflects light.

Referring to FIG. 17, a sealed separation membrane (not shown) for covering the upper openings of the unit number of chamber holes 112 is formed at an upper surface of the micro-chamber body 110. The sealed separation membrane (not shown) is formed by coating and sealing a separation membrane 130 formed of a porous material with polymer oil. The polymer oil may be mineral oil, silicone oil, hydrocarbon oil, paraffin wax or the like. Meanwhile, by coating the separation membrane 130 formed of the porous material with the mineral oil, the optical transparency is increased. The separation membrane 130 may be a polypropylene membrane.

Referring to FIG. 17, the sample solution including nucleic acid and a special component 140 for analyzing the nucleic acid including a primer or a probe are built in each of the unit number of chamber holes 112. A reference numeral 150 is a mixed solution thereof. Other elements which are not described are based on the description in the first embodiment.

Fourth Embodiment

The fourth embodiment relates to an apparatus set for manufacturing a micro-chamber plate with a built-in sample according to the present invention.

Referring to FIGS. 10 and 12, the fourth embodiment includes a micro-chamber plate receiving part 200 in which the micro-chamber plate 100 for sample injection can be settled. An upper opening which settles the micro-chamber plate 100 for sample injection is formed at an upper end of the micro-chamber plate receiving part 200.

Referring to FIGS. 10 and 12, a cover 310 for micro-chamber plate receiving part which covers the upper openings of the micro-chamber plate receiving part 200 is settled at an upper portion of the micro-chamber plate receiving part 200.

Referring to FIGS. 12 and 15, the cover 310 for micro-chamber plate receiving part includes a provisional storing part 312 in which the sample solution can be provisionally stored, and a plate-shaped auxiliary covering part 314 which is formed to be connected with a circumferential surface of the provisional storing part 312.

Referring to FIG. 13, a vessel communication part is formed at a lower surface of the provisional storing part 312. The vessel communication part may be a cutting line 312-1 which is opened by external force. Meanwhile, the auxiliary covering part 314 is formed with a through-hole 314-1 for auxiliary covering part, which passes through upper and lower surfaces of the auxiliary covering part 314.

Referring to FIGS. 11 and 12, a lower surface of the provisional storing part 312 is inserted into the micro-chamber plate receiving part 200, and an upper end of the provisional storing part 312 and the auxiliary covering part 314 are disposed on an upper end of the micro-chamber plate receiving part 200.

Referring to FIGS. 12 and 15, a cover 320 for provisional storing part is attached to an upper end of the cover 310 for micro-chamber plate receiving part. The cover 320 for provisional storing part is attached so that the upper portion of the provisional storing part 312 is closed partially, and the through-hole 314-1 for auxiliary covering part and the rest of the upper portion of the provisional storing part 312 are exposed to the outside through the through-hole 324 for provisional storing part cover.

Other elements which are not described are based on the description in the first embodiment.

Fifth Embodiment

The fifth embodiment relates to a method of manufacturing an analytic micro-chamber plate according to the present invention.

Figure 18:
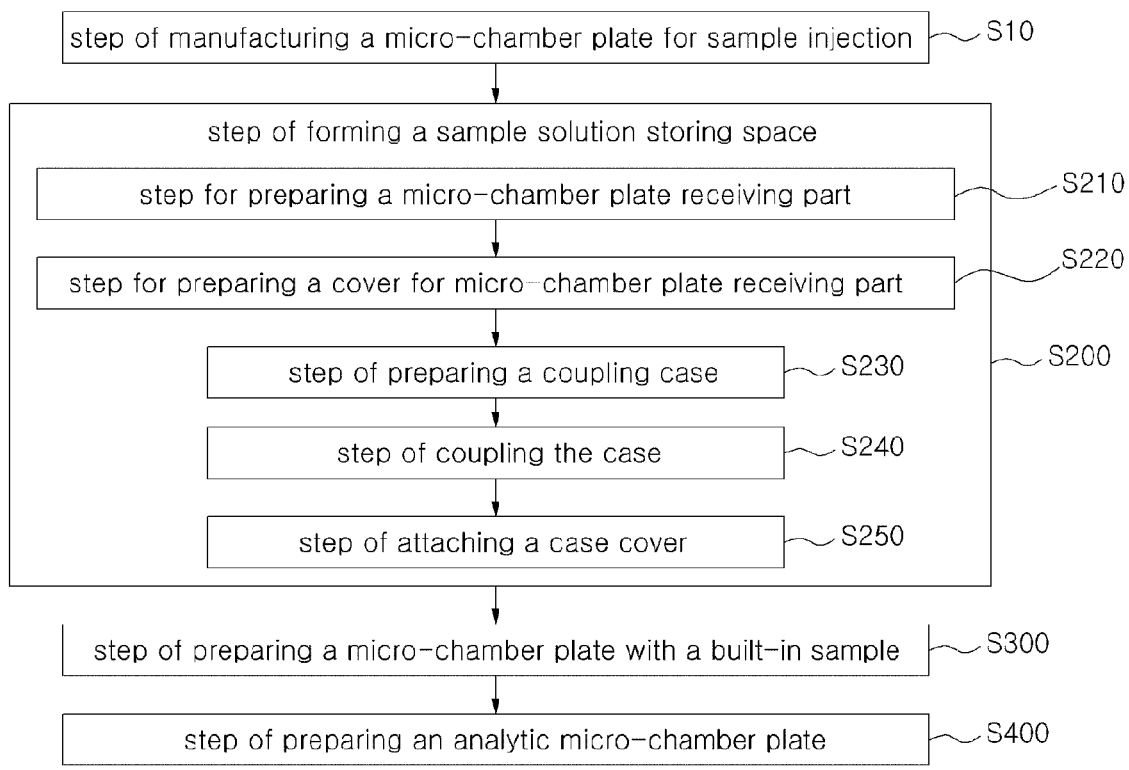
FIG. 18 is a flow chart of a fifth embodiment of the present invention.

Referring to FIG. 18, the fifth embodiment includes a step S100 of preparing a micro-chamber plate for sample injection, a step S200 of forming a sample solution storing space, a step S300 of preparing a micro-chamber plate with a built-in sample, and a step S400 of preparing an analytic micro-chamber plate.

Among them, the step S100 of preparing the micro-chamber plate for sample injection and the step S400 of preparing the analytic micro-chamber plate are based on the description in the first embodiment.

1. Step S200 of Forming a Sample Solution Storing Space

Referring to FIG. 18, the step S200 of forming the sample solution storing space includes a step S210 for preparing a micro-chamber plate receiving part, a step S220 for preparing a cover for micro-chamber plate receiving part, a step S230 of preparing a coupling case, a step S240 of coupling the case, and a step S250 of attaching a case cover.

Figure 19:
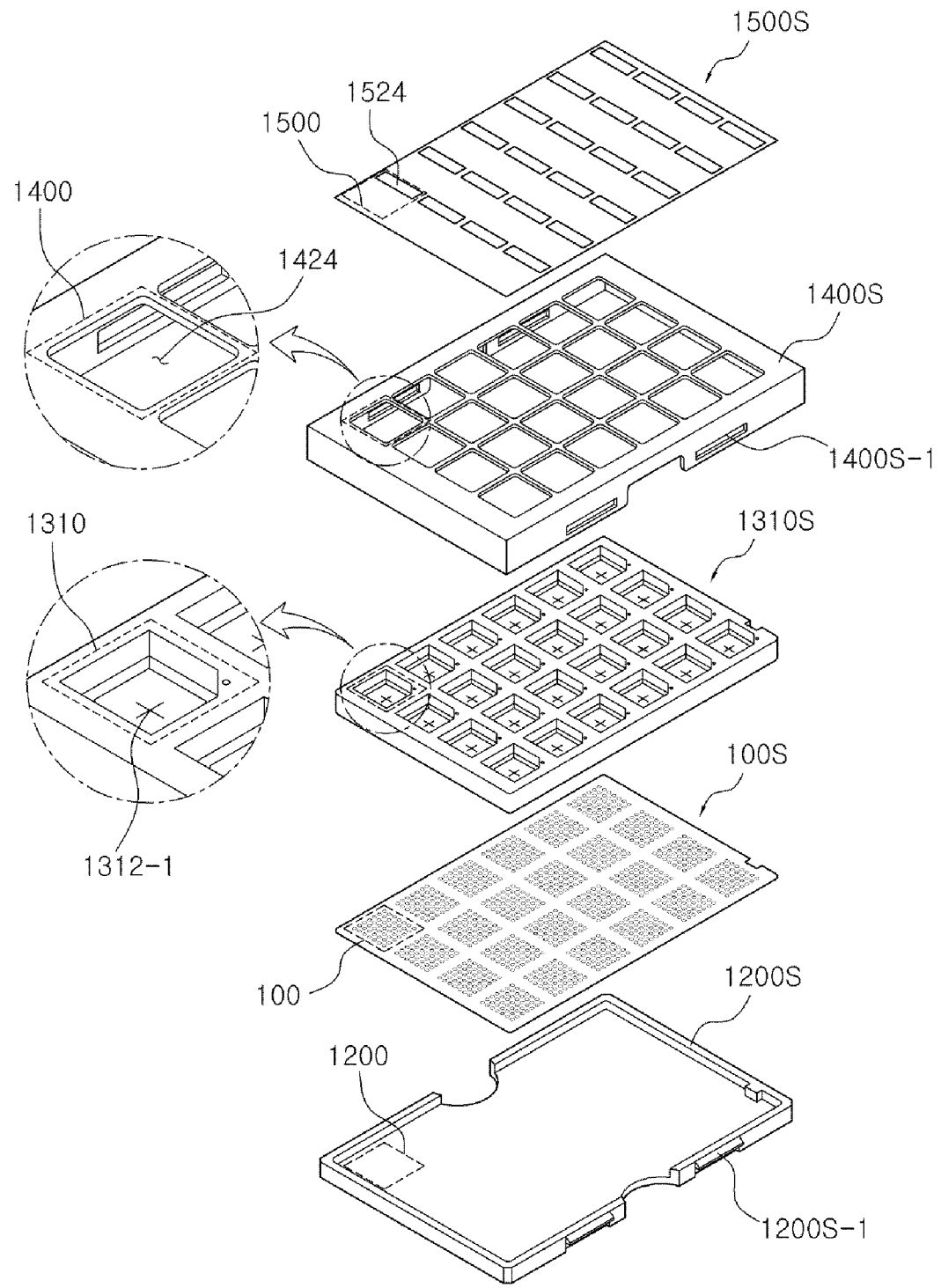
FIG. 19 is an exploded perspective view of explaining a step of forming a sample solution storing space and a step of manufacturing the micro-chamber plate with the built-in sample.
Figure 20:
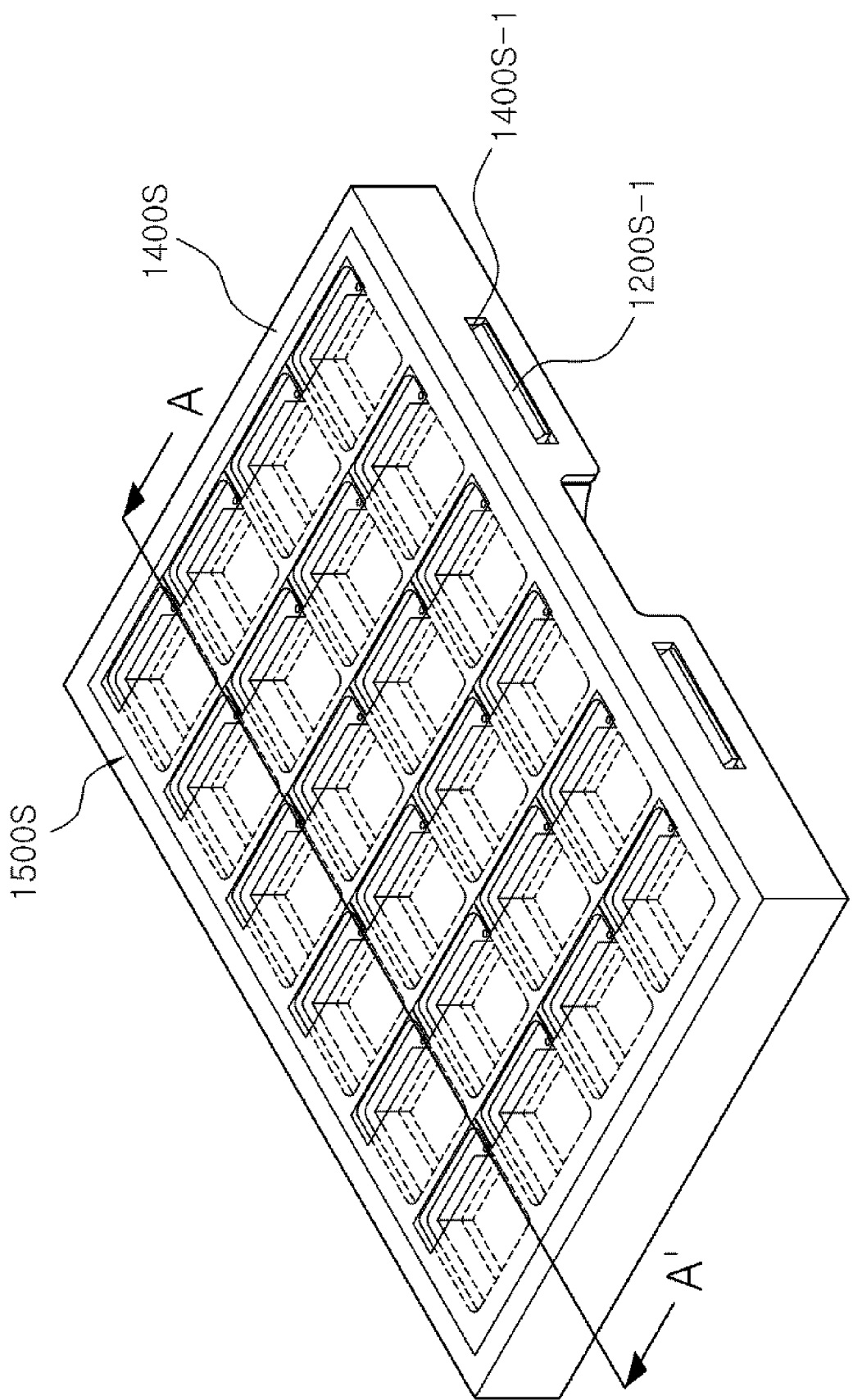
FIG. 20 is an assembled perspective view of FIG. 19.
Figure 21:
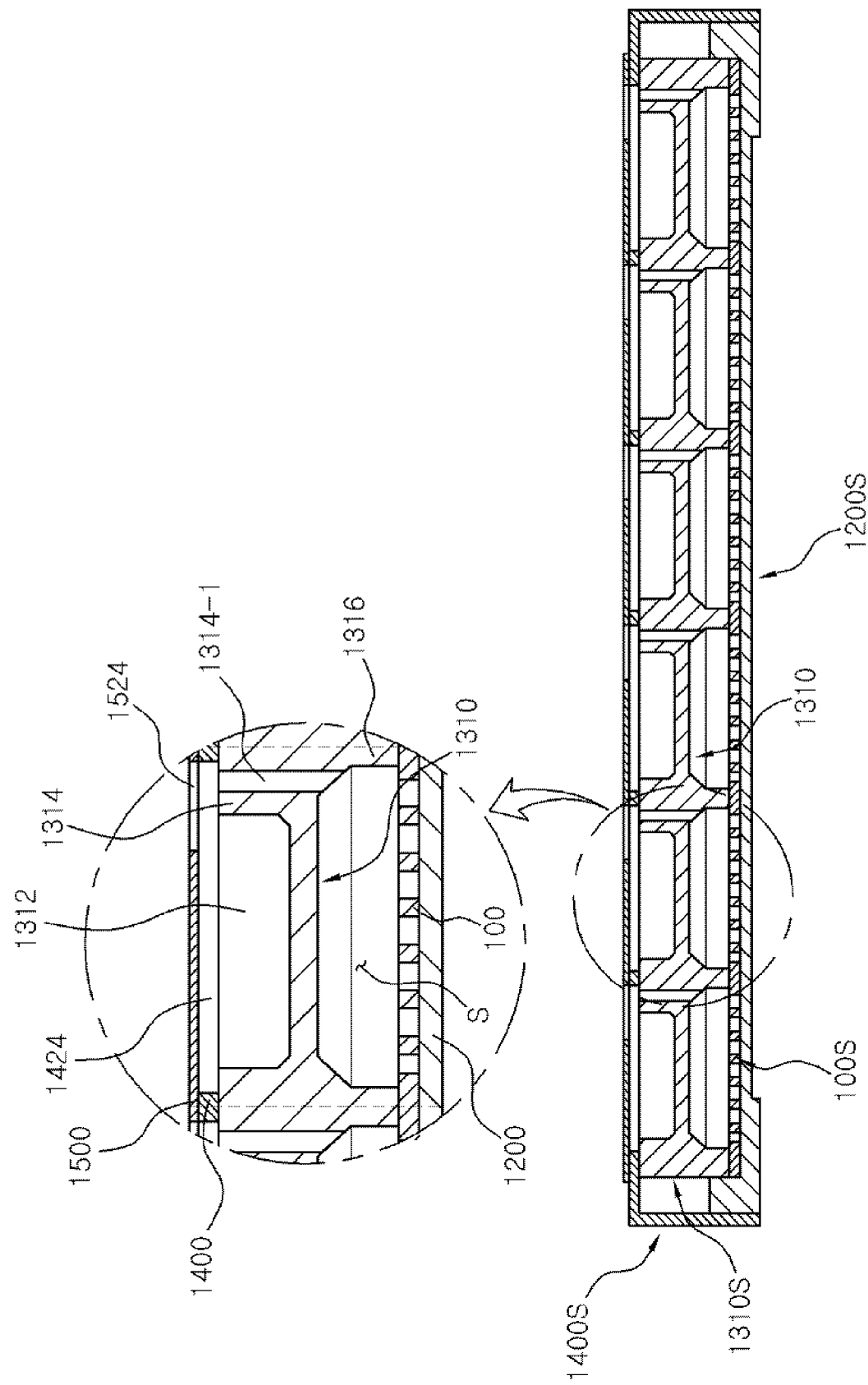
FIG. 21 is a cross-sectional view taken along a line A-A' of FIG. 20.

Referring to FIGS. 19 and 21, in the step S210 for preparing the micro-chamber plate receiving part, a micro-chamber plate receiving part 1200 is formed. The micro-chamber plate receiving part 1200 may be formed into a flat plate shape. The micro-chamber plate receiving part 1200 is to settle the micro-chamber plate for sample injection. A reference numeral 1200S is a micro-chamber plate receiving part set in which multiple micro-chamber plate receiving parts 1200 are formed integrally. Meanwhile, a coupling protrusion 1200S-1 is formed at a side surface of the micro-chamber plate receiving part set 1200S.

Referring to FIGS. 19 and 21, in the step S220 for preparing the cover for micro-chamber plate receiving part, a cover 1310 for micro-chamber plate receiving part, in which a provisional storing part 1312 and an auxiliary covering part 1314 are formed integrally, is prepared. A reference numeral 1310S in FIG. 19 is a cover set for micro-chamber plate receiving part, in which multiple covers 1310 for micro-chamber plate receiving part are connected with each other.

Referring to FIGS. 19 and 21, the provisional storing part 1312 is a vessel which provisionally stores the sample solution including nucleic acid, and a vessel communication part is formed at a lower surface thereof. The vessel communication part may be a cutting line 1312-1 which is opened by external force. The description of the cutting line 1312-1 is based on that in the first embodiment.

Referring to FIGS. 19 and 21, the auxiliary covering part 1314 is formed into a protrusion shape or a plate shape, like in the first embodiment, which is connected to a circumferential surface of the provisional storing part 1312 so as to be arranged horizontally. The auxiliary covering part 1314 is formed with a through-hole 1314-1 for auxiliary covering part, which passes through upper and lower surfaces of the auxiliary covering part 1314.

Referring to FIGS. 19 and 21, a ring-shaped cover supporting part 1316 is formed to be protruded from a lower edge of the cover 1310 for micro-chamber plate receiving part. The cover supporting part 1316 is formed so that a lower end of the through-hole 1314-1 for auxiliary covering part is located in the cover supporting part 1316.

Referring to FIGS. 19 and 21, in the step S230 of preparing a coupling case, a coupling case 1400 which is formed with a through-hole 1424 for case is formed. The through-hole 1424 for case is formed to be communicated with the through-hole 1314-1 for auxiliary covering part and the provisional storing part 1312 when the coupling case 1400 is settled at the cover 1310 for micro-chamber plate receiving part. A reference numeral 1400S in FIG. 19 is a coupling case set in which multiple coupling cases 1400 are connected with each other. Meanwhile, a case coupling groove 1400S-1 in which the coupling protrusion 1200S-1 is inserted is formed at a side surface of the coupling case set 1400S.

Referring to FIGS. 19 and 21, in the step S240 of coupling the case, the coupling case 1400 is pressed to an upper end of the cover 1310 for micro-chamber plate receiving part and then coupled with the micro-chamber plate receiving part 1200. The coupling between the coupling case 1400 and the micro-chamber plate receiving part 1200 is achieved by inserting the coupling protrusion 1200S-1 into the case coupling groove 1400S-1. Since the coupling case 1400 is coupled to the micro-chamber plate receiving part 1200, a lower end of the cover supporting part 1316 is closely contacted with an upper surface of the micro-chamber plate 100 for sample injection, and thus a sample solution storing space S is formed between the cover 1310 for micro-chamber plate receiving part and the micro-chamber plate 100 for sample injection. As the step S240 of coupling the case is performed, a lower end of the through-hole 1314-1 for auxiliary covering part is communicated with the sample solution storing space S, and the through-hole 1424 for case is communicated with the through-hole 1314-1 for auxiliary covering part and the provisional storing part 1312, respectively.

Referring to FIGS. 19 and 21, in the step S250 of attaching the case cover, a case cover 1500 is attached to the coupling case 1400. In order to attach the case cover 1500, an adhesive may be previously applied to the coupling case 1400. The adhesive may be a polymer adhesive, a double-sided tape or the like. The case cover 1500 is formed with a through-hole 1524 for case cover which passes through upper and lower surfaces thereof. The step S250 of attaching the case cover is performed so that the through-hole 1524 for case cover exposes the through-hole 1314-1 for auxiliary covering part to an outside and partially closes the provisional storing part 1312. A reference numeral 1500S in FIG. 19 is a case cover set in which multiple case covers 1500 are connected with each other.

Meanwhile, after performing the step S250 of attaching the case cover, the sample solution including nucleic acid is provisionally stored in the provisional storing part 1312 through the through-hole 1524 for case cover.

2. Step S300 of Preparing a Micro-Chamber Plate with a Built-in Sample

The step S300 of preparing the micro-chamber plate with the built-in sample includes a step of applying vacuum and centrifugal force and a step of releasing vacuum and applying centrifugal force, like in the first embodiment.

In the step of applying the vacuum and centrifugal force, the micro-chamber plate 100 for sample injection and the cover 1310 for micro-chamber plate receiving part are put into a centrifugal separator which can apply vacuum. In this case, referring to FIG. 21,
the through-hole 1524 for case cover is directed upward, and the case cover 1500 is directed to a rotational center of the centrifugal separator, and a bottom surface of the provisional storing part 1312 is directed to an opposite side of the rotational center of the centrifugal separator. Other elements are based on the description of the first embodiment.

Meanwhile, in case of other embodiment, the case cover 1500 which covers the through-hole 1424 for case is attached to the coupling case 1400. The case cover 1500 is formed into a membrane filter which allows penetration of gas but prevents penetration of the sample solution. In this case, the case cover 1500 is not formed with the through-hole 1424 for case. Further, in order to attach the membrane filter as the case cover 1500, an adhesive may be applied to the coupling case 1400. The adhesive may be a polymer adhesive, a double-sided tape or the like.

Meanwhile, in case of other embodiment, the case cover 1500 may be not attached to the coupling case 1400.

Other elements are based on the description of the first embodiment.

Sixth Embodiment

The sixth embodiment relates to a method of manufacturing a micro-chamber plate with a built-in sample.

The sixth embodiment includes a step S100 of preparing a micro-chamber plate for sample injection, a step S200 of forming a sample solution storing space, and a step S300 of preparing a micro-chamber plate with a built-in sample, which are described in the fifth embodiment.

Seventh Embodiment

The seventh embodiment relates to an apparatus set for manufacturing a micro-chamber plate with a built-in sample.

Referring to FIGS. 19 and 21, the seventh embodiment includes a micro-chamber plate receiving part 1200. The micro-chamber plate receiving part 1200 may be formed into a flat plate shape. The micro-chamber plate receiving part 1200 is to settle the micro-chamber plate 100 for sample injection. A reference numeral 1200S is a micro-chamber plate receiving part set in which multiple micro-chamber plate receiving parts 1200 are connected with each other. Meanwhile, a coupling protrusion 1200S-1 is formed at a side surface of the micro-chamber plate receiving part set 1200S.

Referring to FIGS. 19 and 21, the seventh embodiment includes a cover 1310 for micro-chamber plate receiving part in which a provisional storing part 1312 and an auxiliary covering part 1314 are formed integrally. A reference numeral 1310S in FIG. 19 is a cover set for a micro-chamber plate receiving part in which multiple covers for a micro-chamber plate receiving part are connected with each other.

Referring to FIGS. 19 and 21, the provisional storing part 1312 is a vessel which provisionally stores the sample solution including nucleic acid, and a vessel communication part is formed at a lower surface thereof. The vessel communication part may be a cutting line 1312-1 which is opened by external force. The description of the cutting line 1312-1 is based on that in the first embodiment.

Referring to FIGS. 19 and 21, the auxiliary covering part 1314 is formed into a protrusion shape or a plate shape, like in the first embodiment, which is connected to a circumferential surface of the provisional storing part 1312 so as to be arranged horizontally. The auxiliary covering part 1314 is formed with a through-hole 1314-1 for auxiliary covering part, which passes through upper and lower surfaces of the auxiliary covering part 1314.

Referring to FIGS. 19 and 21, a ring-shaped cover supporting part 1316 is formed to be protruded from a lower edge of the cover 1310 for micro-chamber plate receiving part. The cover supporting part 1316 is formed so that a lower end of the through-hole 1314-1 for auxiliary covering part is located in the cover supporting part 1316.

Referring to FIGS. 19 and 21, the seventh embodiment includes a coupling case 1400. The coupling case 1400 is formed with an through-hole 1424 for case, which passes through upper and lower surfaces of the coupling case 1400. The through-hole 1424 for case is formed to be communicated with the through-hole 1314-1 for auxiliary covering part and the provisional storing part 1312 when the coupling case 1400 is settled at the upper end of the cover 1310 for micro-chamber plate receiving part. A reference numeral 1400S in FIG. 19 is a coupling case set in which multiple coupling cases 1400 are connected with each other. Meanwhile, a case coupling groove 1400S-1 in which the coupling protrusion 1200S-1 is inserted is formed at a side surface of the coupling case set 1400S.

Referring to FIGS. 19 and 21, the coupling case 1400 is pressed to an upper end of the cover 1310 for micro-chamber plate receiving part and then coupled with the micro-chamber plate receiving part 1200. The coupling between the coupling case 1400 and the micro-chamber plate receiving part 1200 is achieved by inserting the coupling protrusion 1200S-1 into the case coupling groove 1400S-1. Since the coupling case 1400 is coupled to the micro-chamber plate receiving part 1200, a lower end of the cover supporting part 1316 is closely contacted with an upper surface of the micro-chamber plate 100 for sample injection, and thus a sample solution storing space S is formed between the cover 1310 for micro-chamber plate receiving part and the micro-chamber plate 100 for sample injection. As the coupling case 1400 is coupled with the micro-chamber plate receiving part 1200, a lower end of the through-hole 1314-1 for auxiliary covering part is communicated with the sample solution storing space S, and the through-hole 1424 for case is communicated with the through-hole 1314-1 for auxiliary covering part and the provisional storing part 1312, respectively.

Referring to FIGS. 19 and 21, a case cover 1500 is attached to the coupling case 1400. The case cover 1500 is formed with a through-hole 1524 for case cover which passes through upper and lower surfaces thereof. The through-hole 1524 for case cover is formed so that the through-hole 1314-1 for auxiliary covering part is exposed to an outside and the provisional storing part 1312 is partially closed, when the case cover 1500 is attached to the coupling case 1400. A reference numeral 1500S in FIG. 19 is a case cover set in which multiple case covers 1500 are connected with each other.

Other elements which are not described are based on the description of the fifth embodiment.

INDUSTRIAL APPLICABILITY

According to the present invention as described above, since the separation membrane which is the injection part of the sample solution including nucleic acid is used as the optical measuring part, it is possible to provide a simple structure, prevent measurement error of the optical measuring part due to the contamination, reduce a size of the analytic micro-chamber plate, facilely control the temperature and thus remarkably reduce the analyzing time.

Further, in case that the sample solution including nucleic acid is injected into the chamber hole, since the gas in the chamber hole is firstly removed by using vacuum, and then the injection of the sample solution is performed through the separation membrane, it is possible to completely inject the sample solution within a short time without any remained gas and prevent the error of the optically measured value due to the remain gas. Further since the separation membrane is sealed with the polymer oil such as mineral oil and silicon oil, it is possible to prevent the cross contamination due to the mixing of the solutions in the chamber holes, thereby increasing the analyzing accuracy.

Further, since the multiple analytic micro-chamber plates can be formed integrally, it is possible to compare and analyze various kinds of samples at the same time, thereby remarkably reducing the analyzing time.

Further, since the separation membrane and the other surface of the optical measuring part can be integrally formed with the analytic micro-chamber plate, the analytic micro-chamber plate of the present invention can be manufactured by the compression molding of aluminum or the like, and thus the production process and manufacturing cost can be remarkably reduced.

While the present invention has been described with respect to the specific embodiments, it will be apparent to those skilled in the art that various changes and modifications may be made without departing from the spirit and scope of the invention as defined in the following claims.

The invention claimed is:

1. An apparatus set for manufacturing a micro-chamber plate with a built-in sample, comprising:
   a micro-chamber plate receiving part which is formed with an upper opening;
   a cover for a micro-chamber plate receiving part, which comprises a provisional storing part and an auxiliary covering part connected with the provisional storing part and formed with a through-hole for auxiliary covering part, and which covers an upper opening of the micro-chamber plate receiving part, the provisional storing part being formed with a vessel communication part which can be opened and closed and is communicated with the micro-chamber plate receiving part when being opened; and
   a cover for provisional storing part which exposes the through-hole for auxiliary covering part to an outside and partially closes the provisional storing part.

2. The apparatus set according to claim 1, wherein a lower surface of the provisional storing part is inserted into the micro-chamber plate receiving part, and
   an upper end of the provisional storing part and the auxiliary covering part are disposed at an upper end of the micro-chamber plate receiving part.

3. The apparatus set according to claim 1, further comprising a cover for provisional storing part which covers an upper end of the through-hole for auxiliary covering part and an upper end of the provisional storing part,
   wherein the cover for provisional storing part is a membrane filter which allows penetration of gas and prevents penetration of the sample solution.

4. The apparatus set according to claim 1, wherein the vessel communication part is a cutting line which is opened by external force.

5. An apparatus set for manufacturing a micro-chamber plate with a built-in sample, comprising:
   a cover for micro-chamber plate receiving part, which comprises a provisional storing part and an auxiliary covering part connected with the provisional storing part and formed with a through-hole for auxiliary covering part, wherein a lower end of the cover is closely contacted with an upper surface of a micro-chamber plate for sample injection by coupling means so that a sample solution storing space is formed between the cover for micro-chamber plate receiving part and the upper surface of the micro-chamber plate for sample injection, wherein the provisional storing part is formed with a vessel communication part which can be opened and closed and is communicated with the sample solution storing space when being opened, wherein the coupling means comprises:

a micro-chamber plate receiving part in which the micro-chamber plate for sample injection is settled; and a coupling case of which an upper surface is formed with the through-hole for auxiliary covering part and a through-hole for case communicating the provisional storing part to an outside, and which compresses an upper end of the cover for micro-chamber plate receiving part so as to be coupled to the micro-chamber plate receiving part, wherein the apparatus further comprises:

a case cover which is attached to the coupling case so as to cover the through-hole for case, such that the through-hole is exposed to an outside and the provisional storing part is closed partially.

6. The apparatus set according claim 5, wherein the vessel communication part is a cutting line which is opened by external force.

7. The apparatus set according to claim 5, wherein the case cover is attached to the coupling case so as to cover the through-hole, and the case cover is a membrane filter which allows penetration of gas and prevents penetration of the sample solution.

\* \* \* \* \*